(12) United States Patent
Kirchhoff et al.

(10) Patent No.: US 7,361,143 B2
(45) Date of Patent: Apr. 22, 2008

(54) WEIGHT CONTROL SYSTEM HAVING VARYING MEAL PLANS AND MEAL PLANNING SCHEMES

(75) Inventors: David Kirchhoff, Darien, CT (US); Lisa Connelly, New York, NY (US); Anna Crook, Rozelle (AU); Sheila Kelly, New York, NY (US); Karen Miller-Kovach, Centerport, NY (US); Amie Perl, Short Hills, NJ (US); Palma Posillico, Huntington, NY (US); Thilo Semmelbauer, New York, NY (US); Amy Sheppard, Jersey City, NJ (US)

(73) Assignees: WEIGHTWATCHERS.COM, Inc., New York, NY (US); Weight Watchers International, Inc., Woodbury, NY (US)

( * ) Notice: Subject to any disclaimer, the term of this patent is extended or adjusted under 35 U.S.C. 154(b) by 0 days.

(21) Appl. No.: 10/797,282

(22) Filed: Mar. 10, 2004

(65) Prior Publication Data

US 2004/0210456 A1    Oct. 21, 2004

Related U.S. Application Data

(62) Division of application No. 10/355,425, filed on Jan. 31, 2003.

(60) Provisional application No. 60/353,811, filed on Feb. 1, 2002.

(51) Int. Cl.
*A61B 5/00* (2006.01)

(52) U.S. Cl. ........................... 600/300; 128/921
(58) Field of Classification Search ........... 600/300, 600/301; 128/903–905, 920–921, 898; 434/127; 705/2–4, 10

See application file for complete search history.

(56) References Cited

U.S. PATENT DOCUMENTS

| | | | |
|---|---|---|---|
| 4,686,624 A | 8/1987 | Blum et al. | |
| 5,673,691 A * | 10/1997 | Abrams et al. | 600/300 |
| 5,954,640 A | 9/1999 | Szabo | |
| 6,283,914 B1 | 9/2001 | Mansfield et al. | |
| 6,370,513 B1 * | 4/2002 | Kolawa et al. | 705/10 |
| 6,478,736 B1 * | 11/2002 | Mault | 600/300 |
| 6,513,532 B2 * | 2/2003 | Mault et al. | 128/921 |
| 2002/0072932 A1 | 6/2002 | Swamy | |
| 2002/0097277 A1 | 7/2002 | Pitroda | |
| 2002/0124017 A1 | 9/2002 | Mault | |
| 2002/0133378 A1 | 9/2002 | Mault et al. | |
| 2003/0050802 A1 | 3/2003 | Jay et al. | |

OTHER PUBLICATIONS http://mirror.sg.depaul.edu/pub/usenet-by-group/alt.answers/dieting-faq/part3.*

* cited by examiner

*Primary Examiner*—Max Hindenburg
*Assistant Examiner*—Michael C. Astorino
(74) *Attorney, Agent, or Firm*—St. Onge Steward Johnston & Reens LLC

(57) ABSTRACT

A weight control software system and method may provide an interactive software environment to a user via a network to enhance the ability of users to follow a weight control program. The weight control software system may generate meal plans that are automatically updated based on an updated weight of the user following the weight control program. A variety of tools may be integrated into the weight control software system and be interoperable to utilize information entered by the user or generated by the system in controlling body weight of the user. Such tools may include varying meal plan types and varying schemes for generating meal plans.

27 Claims, 28 Drawing Sheets

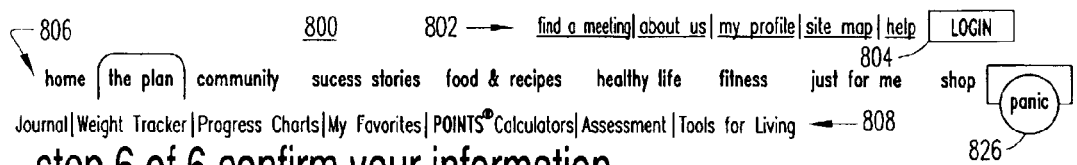

806 — 800 802 — find a meeting | about us | my profile | site map | help  [LOGIN]
804
home | the plan | community  sucess stories  food & recipes  healthy life  fitness  just for me  shop  [panic]
Journal | Weight Tracker | Progress Charts | My Favorites | POINTS® Calculators | Assessment | Tools for Living — 808
826 step 6 of 6 confirm your information

Please confirm that all details you entered are correct. Click the "make changes" link below to make corrections Current Weight Information — 810
    Current Weight: 223lb
    Height: 5'8"
    Gender: M
    Birthdate: 7/14/1966
Make changes to Weight Information Personal Information — 812     814 — Other Characteristics
    First name: John                   Attitude: Generally Happy
    Last name: Smith                   Athletic: Yes
    Address: 1 MAIN St.              Eye color: Blue
    City: Anytown                    Hair color: Brown
    State: NY
    Zip code home: 12345      814 — Other Demographics
    Zip code work: 12346              Race: Caucasian
    Country: United States            Religion: Catholic
    Phone: (212) 555-1234            Ethnicity: Irish
    E-mail: jsmith@workplace.com      Blood type: A+
    Receive Information: No      816
    E-mail Weight Loss Progress: No        Heath Restrictions
    E-mail Format: text      818          None
    Profession: Professional (e.g., doctor,lawyer)
    Marital status: Single            Desired Meal Plan Type
    Number of children: 0              Regular
    Lifetime Member: 98765
    Meeting Member number: 98765
Make changes to Personal Information Payment Information — 822
    Credit Card: Visa
    Credit card number: ************1111
    Expiration date: 2/2002
Name as it appears on the card: John Q Smith
    Billing Address: 1 MAIN St.
    City: Anytown
    State: NY
    Zip code: 12345
Make changes to Payment Information Total Subscription Charges for — 824
    Monthly Fee: $8.00 x 6=: $48.00
    Savings/Discount: $0.00
    Taxes: $0.00
    Total Charges: $48.00

1500a | find a meeting | about us | my profile | site map | help | LOGOUT home · my plan · community · sucess stories | food & recipes | healthy life · fitness · just for me · shop · panic Articles | Recipes | Meal Plans | Recipe Renovation | Recipe Search | Recipe Builder my shortcuts LOGOUT
to weight loss tools.

Welcome Kevin!
I'm not Kevin | edit profile
Pick my avatars!

MY TOOLS
| JOURNAL |
| WEIGHT TRACKER |
| MEAL PLANS |
| POINTS® CALCULATORS |
| RECIPE SEARCH |
| RECIPE BUILDER |

MY RESOURCES
Intro to eTools
Tools for Living
Hot eTools Topic of the Week
Eating Out Guide
eTools Tip
Exchange
                    edit
| Favorite Recipes ▼ |
                    edit
| Favorite Boards ▼ |

MY MEETINGS
75202 | edit
Enter a zip code below
[       ] ▶
Don't know zip code

MY NEWSLETTER & MORE
Choose your options
GET HELP
Frequently Asked Questions
Contact Us meal plans
my 7-day meal plan Using a meal plan is simple way to kick-start your weight loss. Whether you follow the meal plan to the letter or simply use it for ideas and inspiration is up to you. For help using the meal plan, see our meal plan user guide.

next day | weekly view

WED Jan 23 | 23 POINTS        [ update my meal plan ]─1504

☑ MORNING:  [ Swap for another meal? ▼ ]─1502

|  | POINTS |
|---|---|
| Cheese Omlet | 6 |
| ■ 3 medium egg white(s) | 1 |
| ■ 1 tsp basil | 0 |
| ■ 1 oz low-fat cheddar or colby cheese | 1 |
| ■ 1 slice high-fiber bread | 1 |
| ■ 1 cup canned fruit cocktail, packed in water | 1 |
| ■ 1 cup low-fat milk | 2 |

☑ MIDDAY: [ Swap for another meal? ▼ ]

|  | POINTS |
|---|---|
| Veggie Chili | 5 |
| ■ 1 cup Health Valley Mild Vegetarian Chili | 2 |
| ■ 1 cup fresh vegetable sticks | 0 |
| ■ 1 Tbsp reduced-calorie salad dressing | 1 |
| ■ 1 cup grapes | 1 |
| ■ 1 slice toasted wheat bread | 1 |
| ■ 1 Tbsp I Can't Believe It's Not Butter! Fat-Free Margarine | 0 |

☑ EVENING: [ Swap for another meal? ▼ ]

|  | POINTS |
|---|---|
| Apricot Turkey Breast with Cinnamon Squash | 7 |
| ■ 4 oz boneless, skinless turkey breast(s) | 3 |
| ■ 1 Tbsp apricot jam | 1 |
| ■ 1 tsp ground ginger | 0 |
| ■ 3/4 medium acorn squash | 2 |
| ■ 1/8 tsp ground cinnamon | 0 |
| ■ 1 Tbsp light butter | 1 |
| ■ 1 1/2 cup green snap beans | 0 |

☑ SNACK: [ Swap for another meal? ▼ ]

|  | POINTS |
|---|---|
| Snacks and Treats | 5 |
| ■ 1 cup 0-POINT soup | 0 |
| ■ 1 cup fresh vegetable sticks | 0 | need help?
Learn more and answer questions in our meal plan user guide.
■ meal plan user guide
meal planner profile
Plan for | Me-Plan
Special diet | Regular
POINTS range | 22-27
■ edit meal plan profile
■ about meal plans

*FIG. 15A*

806b  1900  find a meeting | about us | my_profile | site map | help  [LOGOUT]

home | my plan | community  sucess stories  food & recipes  healthy life  fitness  just for me  shop  (panic)

Journal Weight Tracker | Progress Charts | My Favorites | POINTS® Calculators | Assessment | Tools for Living | Intro to eTools
— 808b my shortcuts [LOGOUT]
to weight loss tools.

Welcome Kevin!
I'm not Kevin | edit profile
Pick my avatars!

MY TOOLS
| JOURNAL |
| WEIGHT TRACKER |
| MEAL PLANS |
| POINTS® CALCULATORS |
| RECIPE SEARCH |
| RECIPE BUILDER |

MY RESOURCES
Intro to eTools
Tools for Living
Hot eTools Topic of the Week
Eating Out Guide
eTools Tip
Exchange
                    edit
[Favorite Recipes  ▼]
                    edit
[Favorite Boards  ▼]

MY MEETINGS
75202 | edit
Enter a zip code below
[        ] ⊳
Don't know zip code MY NEWSLETTER & MORE
Choose your options GET HELP
Frequently Asked Questions
Contact Us weight tracker  Wednesday, January 16, 2002

| Total weight loss |  Most recent weight: 221.6lbs on 1/14/2002
| 🏋 10.0 LBS. | POINTS Range: 22-27
|  | Meeting day: Monday  ╲ 1902

Milestones: ☆ 5

| Thank You                    (📊) VIEW PROGRESS CHARTS |

Thank you for logging your weight this week!
Please return next Monday to log your weight.
Share stories on Tales from the Scale

⊳ ENTER PREVIOUS WEIGHT health & safety        getting to              learn more,
                           weight goal             weigh less we put your              Whether                     Make the
          health and               you lost big                scale your
          safety first.            this week or                friend each
          Learn about              were a little               week by
          how your                 disappointed,               getting tips
weight and weight-        remember to take           from weight-loss
loss efforts can affect   time out to get            experts and fellow
your health.              insired all over           dieters alike!
■ What's your BMI         again.                     ■ The Great Weigh-In
■ Effects of Rapid Weight ■ 18 Ways to Reward        ■ 20 Weight Loss Tips
Loss                      Yourself                   (from Real Meeting-
                          ■ Create a Motivating      Goers!)
                          Strategy ■ Main
■ View & Edit Weights
■ Enter Previous Weights
■ Additional Information weight loss profile
■ Starting weight: 223
■ 10% difference: 200.7
■ Weight goal: 150.9
■ Weight lost: 2
■ Edit My Profile Beyond the scale
Get a better grip on your
weight-loss success the next
time you carry groceries.
Click the pounds to see what
you'd have to lift.

1lb | 5lb | 10lb | 25lb

[ 4 sticks of butter ]

Change your country
Terms & Conditions | Privacy | For subscribers only: Subscription Agreement

WEIGHT CONTROL SYSTEM HAVING VARYING MEAL PLANS AND MEAL PLANNING SCHEMES

RELATED APPLICATIONS

This patent application is a divisional of currently pending U.S. patent application Ser. No. 10/355,425, filed Jan. 31, 2003, which application claims the benefit of, under Title 35, United States Code, Section 119(e), U.S. Provisional Patent Application No. 60/353,811, filed Feb. 1, 2002.

FIELD OF THE INVENTION

The principles of the present invention are generally related to weight control, and more specifically, but not by way of limitation, to a software and hardware system operable to enable weight control.

BACKGROUND OF THE INVENTION

People have long sought ways to control (i.e., lose, gain, and/or maintain) body weight. Controlling body weight has many implications to people's lives, including: physical health, mental health, and professional and social status. Entire industries have been formed to assist individuals who seek assistance in weight control. Such industries include medical care, food production, publishing, workout facilities, and support groups, to name a few.

Weight control programs (e.g., diets) to control body weight have been developed by many individuals, groups, and organizations and disseminated throughout the different industries. Some of the weight control programs may be considered proprietary and others are publicly available. For example, medical organizations may provide patients with weight control programs that have been developed for patients, but not made publicly available otherwise. Developers of weight control programs earn money by making the programs publicly available through various sources, including books, videos, lectures and tapes, for example. And, of course, the rules of weight control programs and the food types that they prescribe are all different. The diversity of different weight control programs throughout the weight loss industry is considerable: diets range from those ordered by a physician as part of a treatment for a disease or clinical condition to calorie-counting diets, vegetarian diets, protein rich diets, sodium gram diets, fluid-restricted diets, renal diets (which utilize fluid, protein and specific electrolyte restrictions such as sodium, potassium, etc.) and cardiac diets (which utilize specific fat, salt, and cholesterol restrictions).

No matter which of the various sources a developer of a weight control program utilizes to make its weight control program publicly available or which type of diet the weight control program utilizes, it is the responsibility of the individual following the weight control program to adhere to the rules, guidelines, and conventions (general rules) of the weight control program. These rules may define the specific foods, times to eat and exercises to be performed, for example. And, as most individuals who have followed a weight control program can testify, in addition to maintaining self-motivation, learning and following these often complex rules tend to be the most difficult parts of staying on, and achieving success with, a weight control program. What is needed is a way to provide dieters with the ability to maintain food consumption within the general rules of a weight control program and to maintain motivation in following these rules.

SUMMARY OF THE INVENTION

To overcome the problems of having to follow the complex general rules of a weight control program and to promote self-motivation to adhere to such a weight control program, a software and hardware system has been developed that allows users to actively participate in following a weight control program. A weight control software system, which is provided by a weight control software provider, provides an interactive software environment (weight control software system) delivered via a network. The weight control software system provides and enhances the ability of users to follow a weight control program.

The weight control software system includes several different software modules and tools (e.g., a journal, a weight tracker, a meal planner), which (i) are highly interactive and personalized according to personal user input and individualized feedback produced by the weight control software system based on personal user input, and (ii) possess a high level of interoperability and interconnection within the interactive software environment and underlying architecture (including the modules and tools) such that user input in one module or tool may update other modules and tools for increased user efficiency and personalization.

The specific rules of any weight control program employed by the weight control software system, or any other element of the weight control program, may be delivered to the user either (i) from external sources independent of the weight control software system (e.g., from books, videos, counseling, lectures, and standalone software), or (ii) exclusively via the weight control software system. Regardless of whether these rules or other elements of a weight control program are delivered by independent, external sources or solely by the weight control software system, the rules are incorporated into the weight control software system and govern the functionality of the underlying modules and tools. Accordingly, the overall weight control process is automatic and seamless so that the user is able to focus on the ultimate goal, which is controlling body weight via the weight control program as operated by the weight control software system.

BRIEF DESCRIPTION OF THE DRAWINGS

A more complete understanding of the method and apparatus of the present invention may be obtained by reference to the following Brief Description when taken in conjunction with the accompanying Drawings wherein:

FIG. 8 is an exemplary graphical user interface (e.g., web page) showing one of the various areas of the weight control software system of FIGS. 2-5 whereby users input personal information;

FIG. 11 is another exemplary web page of the journal of FIG. 9 illustrating the integration of exercises from an exercise database of FIG. 5 into the journal consistent with the general rules of the weight control program of FIG. 1;

FIG. 12 is another exemplary web page of the journal of FIG. 9 illustrating the integration of food from a food database of FIG. 5 into the journal consistent with the general rules of the weight control program of FIG. 1;

FIG. 15A is an exemplary web page showing a single day of a multiple-day meal plan of FIG. 14;

FIG. 19 is an exemplary web page of a weight tracker module of FIG. 5 providing the user of the weight control software system with weight tracking capability and individualized feedback;

FIG. 23 is an exemplary web page of the weight control software system of FIG. 2 illustrating the ability of the user to generate public profile information and selectively make that information public;

DETAILED DESCRIPTION OF AN EMBODIMENT OF THE INVENTION

I. Overview of Weight Control Software System

Figure 1:
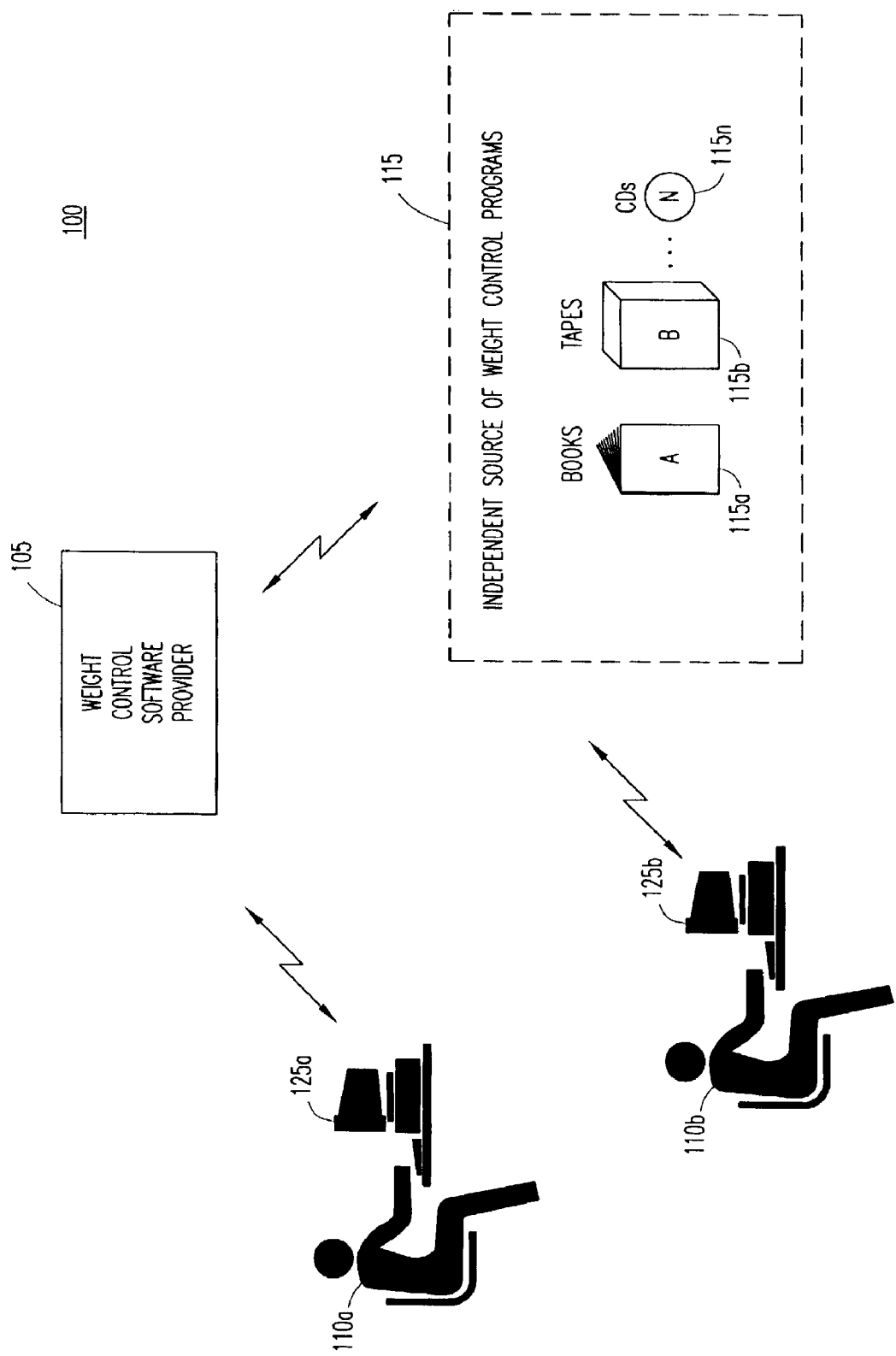
FIG. 1 is an exemplary diagram illustrative of (i) the interaction between users and a provider of a weight control software system that provides the general rules and other elements of any weight control program via the weight control software system, and (ii) the interaction among (a) users, (b) an external source that provides users with the general rules and other elements of any weight control program, and (c) the weight control software provider, in each case according to the principles of the present invention.

FIG. 1 is an exemplary diagram illustrative of (i) interaction between a weight control software provider 105 and users 110a-110b, (collectively 110), where the weight control software provider 105 provides the general rules and other elements of any weight control program 115a-115n (collectively 115) via a weight control software system, and (ii) interaction among (a) users 110, (b) an external source that provides users with the general rules and other elements of the weight control program 115, and (c) the weight control software provider 105 that provides the weight control software system, in each case according to the principles of the present invention. The weight control software system is accessed via the computing systems 125a or 125b (collectively 125) by the users 110a or 110b, respectively.

The weight control program 115 may be any dietary system or technique that allows the user 110 to lose, maintain, or gain body weight. The weight control program 115 may be designed and developed by any entity (including the user 110 him/herself) and may have different rules, guidelines and conventions. These general rules may be provided to the user 110 either directly by the weight control software system via downloading over a network or through external sources, such as, but without limitation, books, tapes, lectures or CD-ROMs.

II. Hardware, Software and Database Structure

Figure 2:
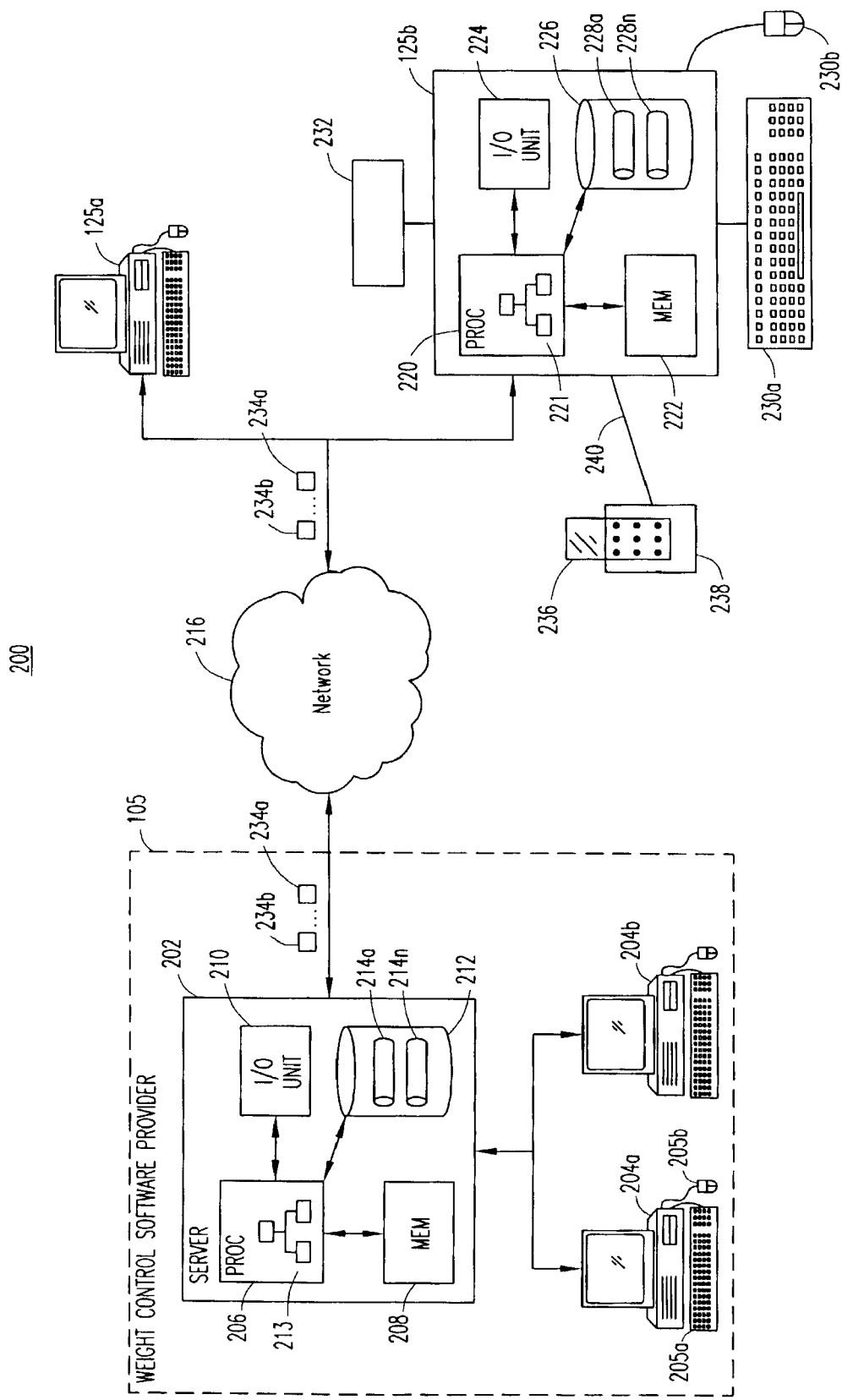
FIG. 2 is an exemplary block diagram for operating a weight control software system for the weight control software provider and users of FIG. 1.

FIG. 2 is an exemplary block diagram 200 for operating a weight control software system for the weight control software provider 105 and users 110 of FIG. 1. The weight control software provider 105 utilizes a server 202 for managing and maintaining the weight control software system or a portion thereof (e.g., databases may be located externally from the server 202).

As is understood in the art, remote terminals 204a and 204b (collectively 204) are operable by the weight control software provider 105 to interact with the server 202 to maintain the weight control software system. The server 202 includes a processor 206 coupled to a memory 208. The processor 206 is further coupled to an input/output (I/O) unit 210 and storage device 212. The storage device 212 may store one or more server database 214a-214n that include data associated with the weight control software system provided by the weight control software provider 105. Server software 213 is operable to maintain and distribute data composed as datasets associated with individual users 110 of the weight control software system.

The server 202 is coupled to a network 216. The network 216 may be any network. The network 216, for example, may be the Internet, a satellite communications network, a wireless or wired telecommunications network, local area network (LAN), wide area network (WAN), or any combination thereof. Additionally, the computing systems 125 utilized by the users 110 are coupled to the network 216. As shown, the computing system 125b includes a processor 220 operating software 221 coupled to a memory 222. The software 221 may include an interface (e.g., a web browser) as understood in the art and facilitate interface and execution with the server software 213 for the user 110 to utilize the weight control software system. The weight control software system may provide for a weight control program 115 (FIG. 1) by storing rules of one or more weight control program 115 on the storage device 212. The weight control software system may thereafter read and logically follow the rules of the weight control program 115 as understood in the art. The processor 220 is further coupled to an I/O unit 224 (e.g., modem) and a storage device 226. The storage device 226 may store user databases 228a-228n (collectively 228), where the user databases 228 may include data that is a subset of the server databases 214.

The computing system 125b further includes input control devices 230a and 230b, such as a keyboard and computer mouse, for operating the weight control software system. A display 232 is also coupled to the computing system 125b for display of information provided by the weight control software system. While the computing systems 125 are shown as desktop computing systems, it should be understood that laptop, other configured computing systems, or terminals (e.g., interactive televisions) may be utilized. It should further be understood that handheld electronic devices, such as mobile wireless devices (e.g., mobile telephones) and personal digital assistants (PDA), may be utilized by the users 110.

In operation, the users 110 utilize the computing system 125 for executing and utilizing the weight control software system. As is understood in the art, the user 110 using the software 221 and associated hardware (e.g., I/O unit 224) may connect to the server 202 via the network 216. Data packets 234a and 234b (collectively 234) are utilized to communicate data of the weight control software system across the network 216 from the server 202 to the computing systems 125 and vise versa. The server 202 may host a website that supports the weight control program 115 (FIG. 1) and provide access to the user 110. The data communicated across the network 216 may include web pages and weight control data stored in the server databases 214 to the computing systems 125 for storage or utilization thereby.

The web pages may be displayed on the display 232, and utilize the data stored in the user databases 228 to allow the user 110 to monitor and maintain the weight control data associated with the weight control program 115. The network interaction between the user 110 and the weight control software provider 105 provides the users 110 with a means for interactively and dynamically adhering to the weight control program 115.

Figure 7:
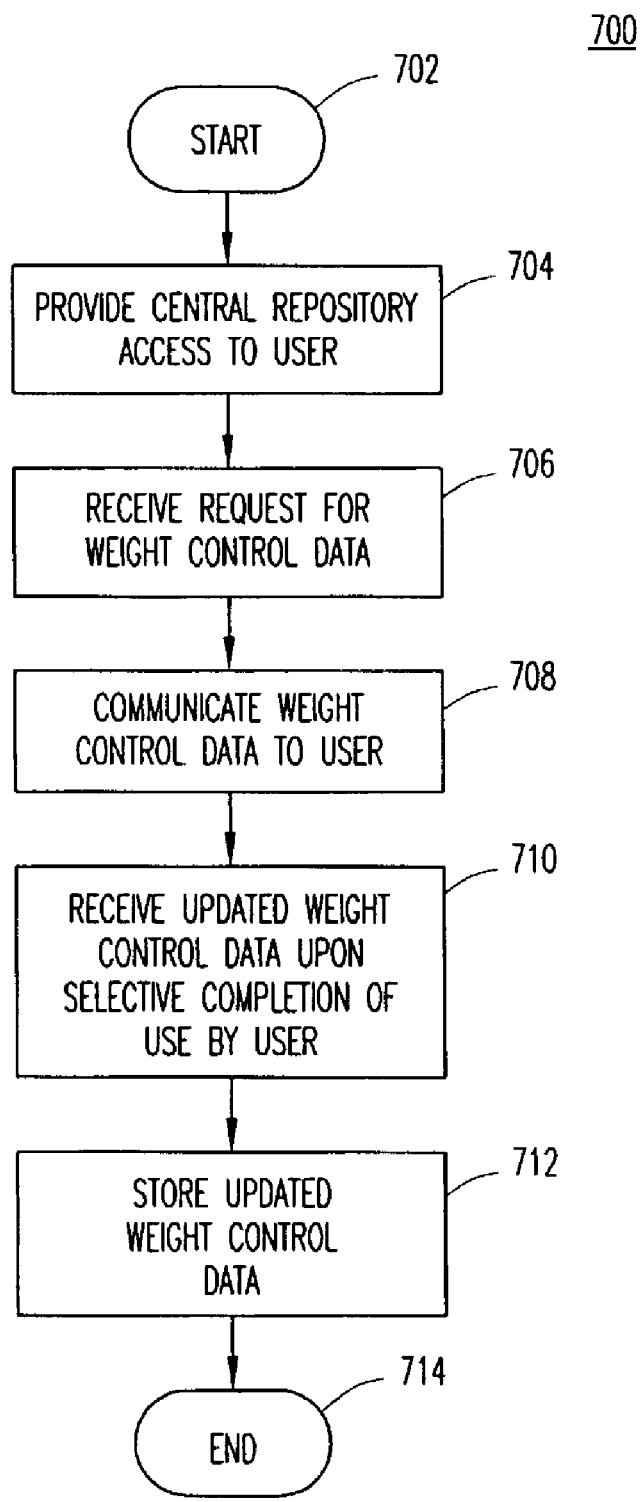
FIG. 7 is an exemplary flow diagram illustrating the process whereby data from the food and exercise databases of the weight control software system of FIGS. 3-5 reside on the computing system of the user, providing the user with quicker and more seamless navigation of the journal of FIG. 9.

To provide the user 110 with a sense that the weight control software system operates faster and/or locally, data may be downloaded from the server 202 to the computing system 125. FIG. 7 is an exemplary flow diagram 700 for providing the user 110 a sense that the weight control software system resides on the computing system 125b of the user 110. Generally, to provide the sense that the weight control software system resides locally, weight control data associated with a user 110b from the server 202 is downloaded to the computing system 125b, updated by the user 110 while the user 110 is logged onto the weight control software system, and communicated back to the server 202 as updated at the end of the session. Alternatively, the weight control software system may be hosted by the server 202.

A consumer, non-network required version of the weight control software system may be provided to the computing system 125b of the user 110 via downloading across the network 216 or reading from a storage medium (e.g., compact disk). The non-network required version may operate independent of a network connection. In one embodiment, a hand-held computing device 236 may communicate with the computing system 125b by a cradle 238 coupled via a wire 240 and may operate the weight control software system independent of or in communication with the network 216. The hand-held computing device may be a personal digital assistant, hand-held personal computer, wireless telephone, or other electronic device capable of executing the weight control software system or a reduced version derived therefrom. The hand-held computing device 236 may be synchronized with the information from the computing system 125b as understood in the art. Accordingly, the hand-held computing device 236 may be capable of downloading data of the user 110, updating the data, and uploading the data for use and/or storage and communication by the computing system 125b.

Referring again to FIG. 7, the process starts at step 702. At step 704, access to the server databases 214 or central repository is provided to the user 110. At step 706, a request for weight control data associated with the user 110 is received. The request may be generated from the user 110 logging onto the weight control software system via the network 216. At step 708, weight control data is communicated to the user 110. The weight control data may be an entire dataset associated with the user 110 or simply a portion thereof. The weight control data may include any data directly or indirectly associated with the user 110. The user 110 may work with the weight control software system to update the data that is temporarily located at the computing system 125b using cache memory or other storage unit. By allowing the user 110 to modify and update the data on the computing system 125b (without further accessing the server 202 during the login session), the user 110 experiences a fast and efficient working environment such as would be experienced if the weight control software system were operating as a standalone or resides (e.g., compact disk based) on the computing system 125b. Upon completion of the session, the user logs-off of the weight control software system and the data may be communicated back to the server 202 via the network 216. At step 710, updated weight control data is received upon selective completion of use of the weight control software system by the user 110. The updated weight control data is stored at step 712, and the process ends at step 714.

Figure 3:
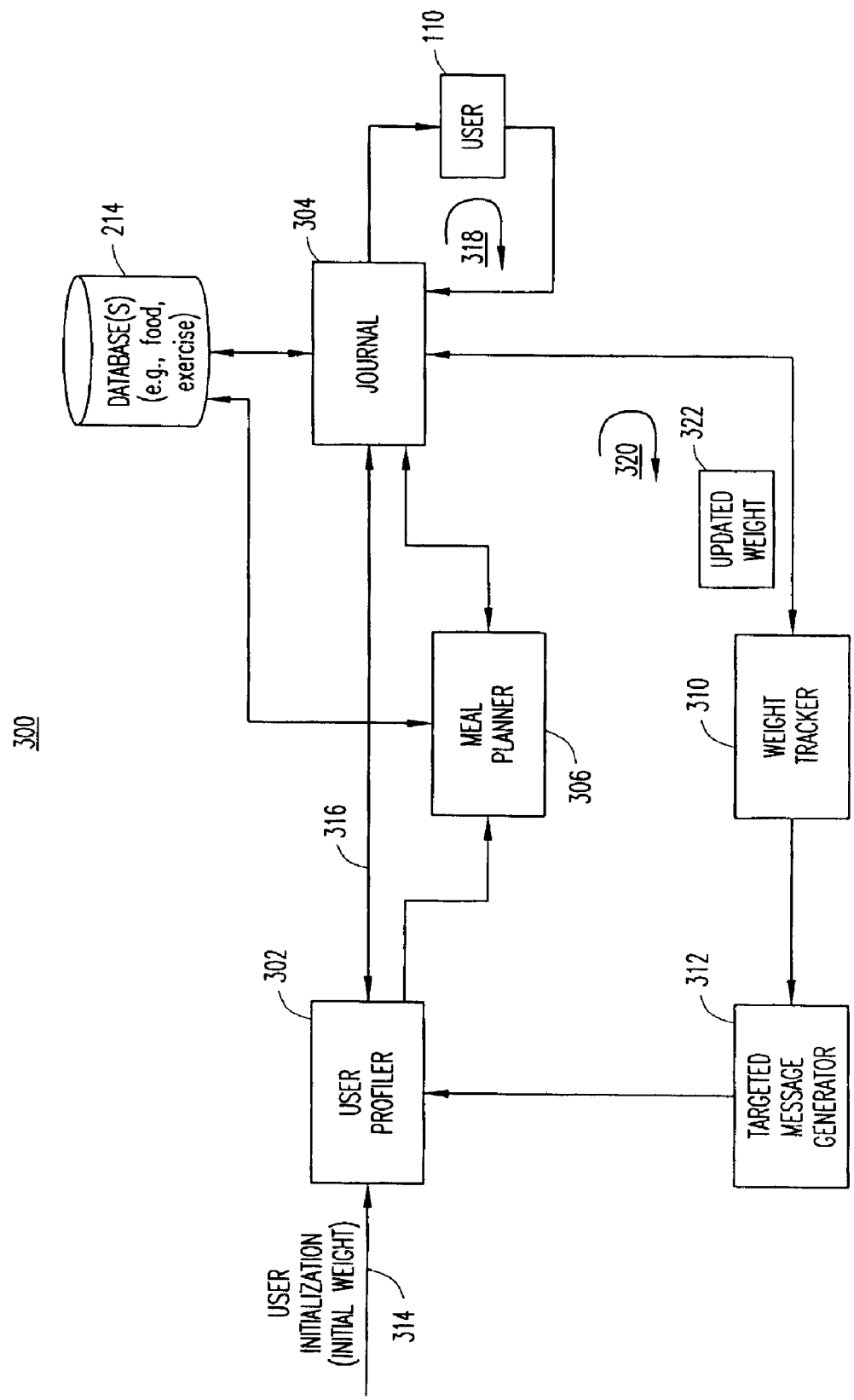
FIG. 3 is an exemplary block diagram that models the processes of the weight control software system of FIG. 1 whereby the weight control software system utilizes personal information as input by a user to (i) customize the weight control software system, (ii) provide the user with individualized feedback and (iii) update the interactive software environment and underlying architecture in accordance with the principles of the present invention.
Figure 4:
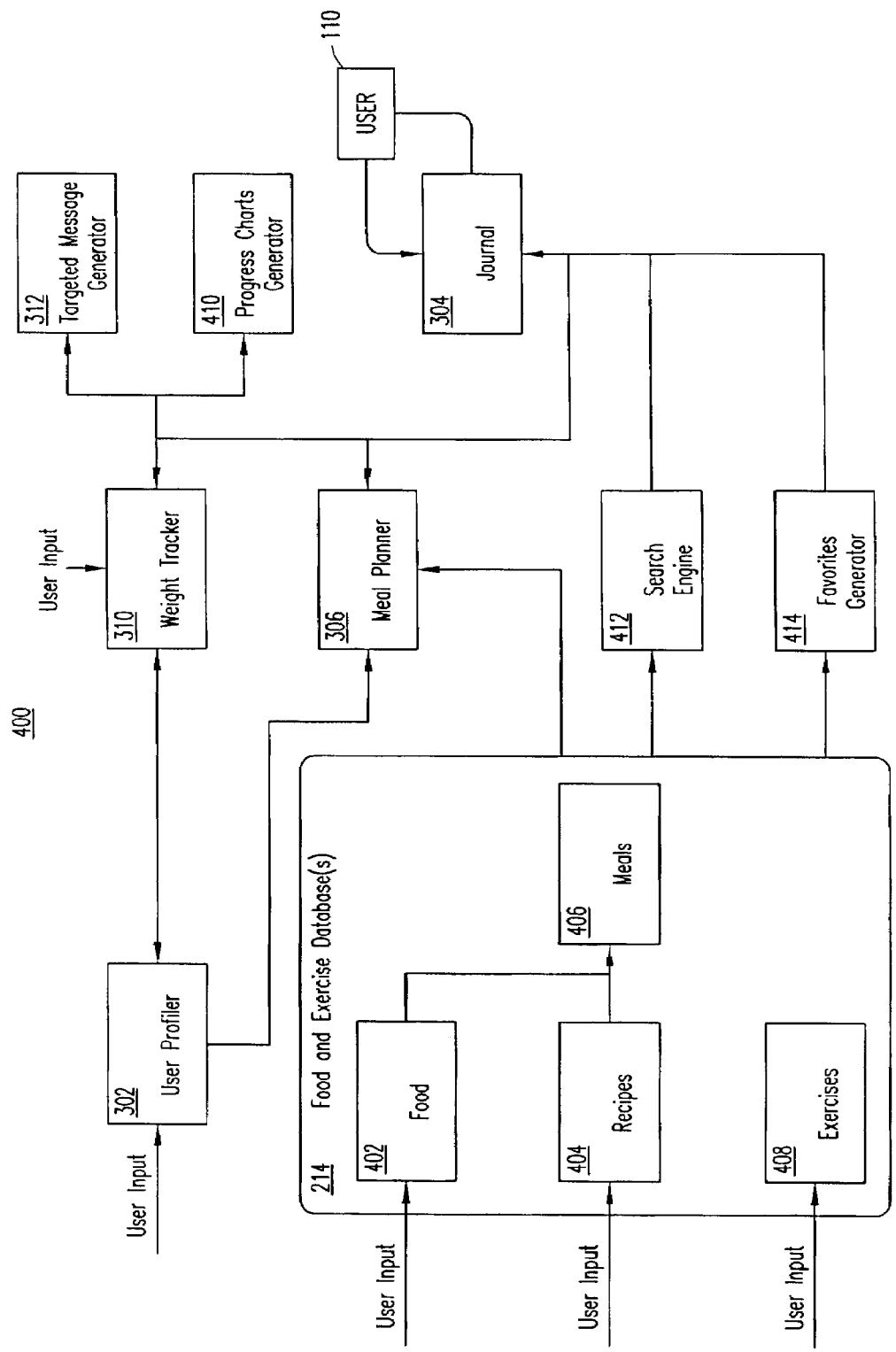
FIG. 4 is a more detailed exemplary block diagram of underlying architecture components of the weight control software system of FIG. 3, including the modules and tools, to utilize personal user input to (i) customize the weight control software system, (ii) provide individualized feedback, and (iii) update the interactive software environment and underlying architecture in accordance with the principles of the present invention.

III. User Personalization of and Interaction with the Weight Control Software System FIGS. 3 and 4 are exemplary block diagrams that model the process, whereby the weight control software system utilizes personal data that is input by the user 110 to (i) customize the weight control software system, (ii) provide the users 110 with individualized feedback, and/or (iii) update the interactive software environment and underlying architecture. The weight control software system manages personal data for a given user 110 that is stored on the server 202. As users 110 enter personal information into the user profiler 302 and subsequently update or include additional information in the weight control software system, the user 110 individualizes the weight control software system and updates certain tools and modules of the weight control software system according to such personal information. The customized weight control software system further aids in the control of body weight by providing feedback to users 110 based on their individual progress utilizing the applicable weight control program 115.

As shown in the block diagram 300 and as described in greater detail in the discussion of FIG. 5 below, a number of components of the model representative of the operation of the weight control software system are configured in an inter-relational manner so as to provide the user 110 with personalization and feedback capabilities. As shown, a user profiler 302 is interconnected directly to a journal 304 and interconnected via a meal planner 306. The server databases 214 may be interconnected to both the journal 304 and meal planner 306 so as to more globally provide access to the data or information stored in the server databases 214. A weight tracker 310 is interconnected to the journal 304 and additionally interconnected to a targeted message generator 312. The targeted message generator 312 may further be interconnected to the user profiler 302. The user profiler 302, journal 304, meal planner 306, server databases 214, and weight tracker 310 may provide the user 110 with the capability of utilizing and maintaining data provided or pre-established by the weight control software provider 105 (FIG. 1) and user-entered data.

Again referring to FIG. 3, the weight control software system utilizes personal information entered by the user 110 to (i) customize the weight control software system, (ii) provide the users 110 with individualized feedback, and/or (iii) update the interactive software environment and underlying architecture. As shown, two feedback loops 318 and 320 are provided in the block diagram 300. Feedback loop 318 may be considered a periodic (e.g., daily) loop that is generated as the user 110 works with the journal 304. Alternatively, the feedback loop 318 may be considered event driven as the weight control software system is utilized by the user 110. The journal 304 provides a constant reminder and motivator for the user 110 to maintain, manage, and adhere to the weight control program 115 (FIG. 1). In other words, the user 110 is provided daily feedback and reminders by simply working with the journal 304 and the information provided therein.

Although the journal 304 and meal planner 306 are shown to be coupled, the components of the weight control software system may be provided to the user 110 by the weight control software system individually and independently. By allowing the components to operate individually and independently, the user 110 may be provided a more limited scope of functionality, but have suitable functionality for the purposes desired by the user 110.

Feedback loop 320 may be considered a periodic or aperiodic feedback loop that is formed by the user 110 performing a weigh-in, where the weigh-in measures the current or updated weight 322 of the user 110. The updated weight 322 may be supplied by the user 110 to the weight tracker 310, which utilizes the updated weight 322 to determine the progress of the user 110.

Figure 6:
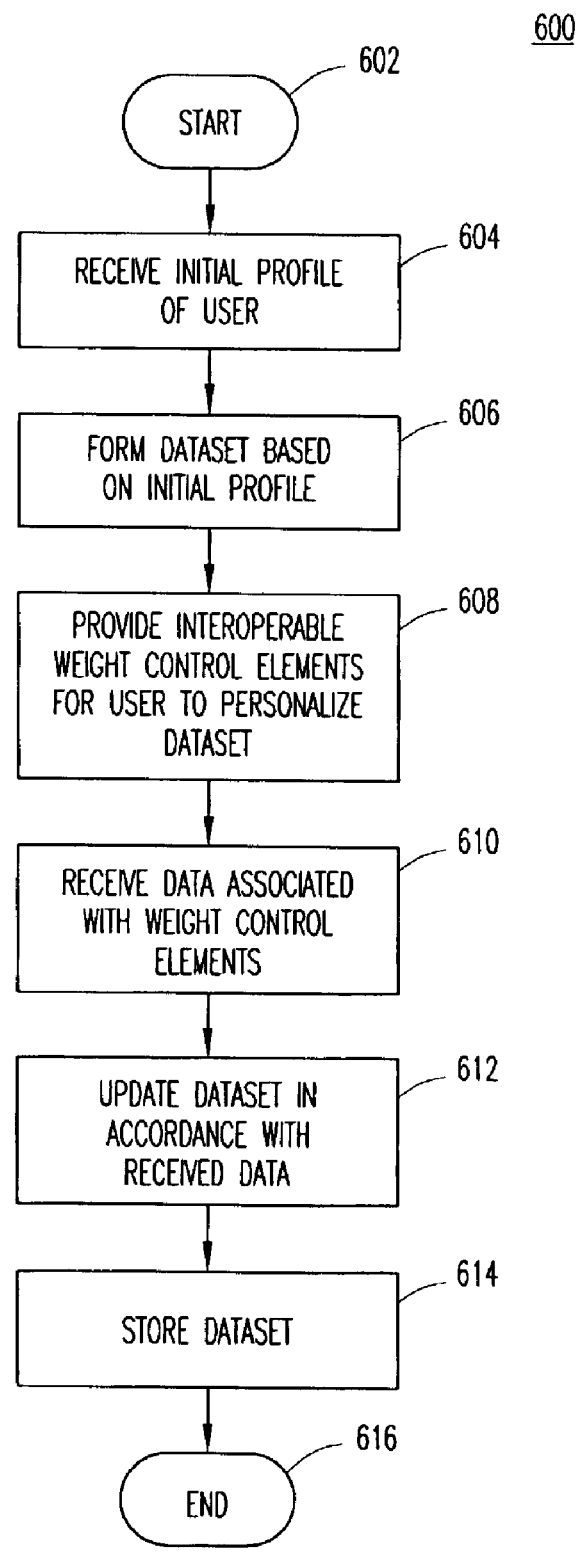
FIG. 6 is an exemplary flow diagram for providing interoperable elements to the user of the weight control software system of FIGS. 2-5 to personalize weight control data.

FIG. 6 is an exemplary flow diagram 600 for providing interoperable elements to the user 110 of the weight control software system to personalize data. An interface for the user 110 to the weight control system may be a graphical user interface, such as a website. The process starts at step 602. At step 604, the initial profile of the user 110 is received. At step 606, a dataset (i.e., weight control data) based on the initial profile of the user 110 is formed. The dataset may include a predetermined meal plan (e.g., list of meals) and other weight control data. Interoperable weight control elements are provided to the user 110 to personalize the dataset for the user 110. The interoperable weight control elements may include hyperlinks, buttons, text boxes, radio buttons, and/or any other user-selectable software interface element as understood in the art. At step 610, data associated with the weight control elements is received.

At step 612, the dataset may be updated in accordance with the received data. The dataset is stored at step 614, and the process ends at step 616. It should be understood that while the user-selectable software elements provided to the user 110 via a web page, for example, are interoperable (i.e., data entered in association with one software element may be accessed by other software elements), the underlying architecture of FIGS. 3-5 provides the interoperability therefor. Such interoperability and interconnection is described in detail in Section IV below.

IV. Interoperability and Interconnection of the Weight Control Software System

FIG. 4 is a more detailed exemplary block diagram 400 of underlying architecture components of the weight control software system of FIG. 3. As shown, the components (e.g., journal, databases, meal planner) of the weight control software system are modular and interoperable. In other words, the information provided to one of the components is accessible to each of the other components.

The server databases 214 have been expanded to show a number of different databases, including food 402, recipes 404, meals 406 and exercises or activities 408. Each of these databases may include pre-established data provided by the weight control product provider 105 (FIG. 1) and user-entered data provided by the user 110. The food database 402 may include food served by restaurants, such as McDonald's® and other brand name restaurants and food products. In addition to the targeted message generator 312, the user 110 is able to utilize a progress chart generator 410 to monitor parameters and/or performance indicators that are indicative of the progress of the user 110 in following the weight control program. For example, the progress chart generator 410 may receive updated weights from the weight tracker 310 and display the updated weights over a period of time so that the user 110 can monitor weight loss, for example. By graphically monitoring or feeding-back weight loss progress, the user 110 may find additional motivation. The graphical representation may additionally allow the user 110 to identify successful periods (e.g., weeks) of weight loss so that the user 110 may review the journal 304 to determine what meals made those periods successful.

Two additional components that are included in the more detailed block diagram 400 of the weight control software system are a search engine 412 and a favorites generator 414. The search engine 412 allows the user 110 to search the server databases 214 for particular words and/or food values. The search engine 412 may be more comprehensive and allow the user 110 to search for types of foods, courses, or any other information that may be stored in the server databases 214 as understood in the art. The favorites generator 414 allows the user 110 to identify and categorize individual foods, meals, recipes, and/or exercises that the user 110 often uses. By including both of these components, the user 110 is able to save time in utilizing the weight control software system. Additionally, the user 110 is able to further customize the weight control software system according to personal desires.

The weight control software system possesses a high level of interoperability and interconnection within the interactive software environment and underlying architecture (including the modules and tools) such that user input in one module or tool may update other modules and tools for increased user efficiency and personalization.

Figure 5:
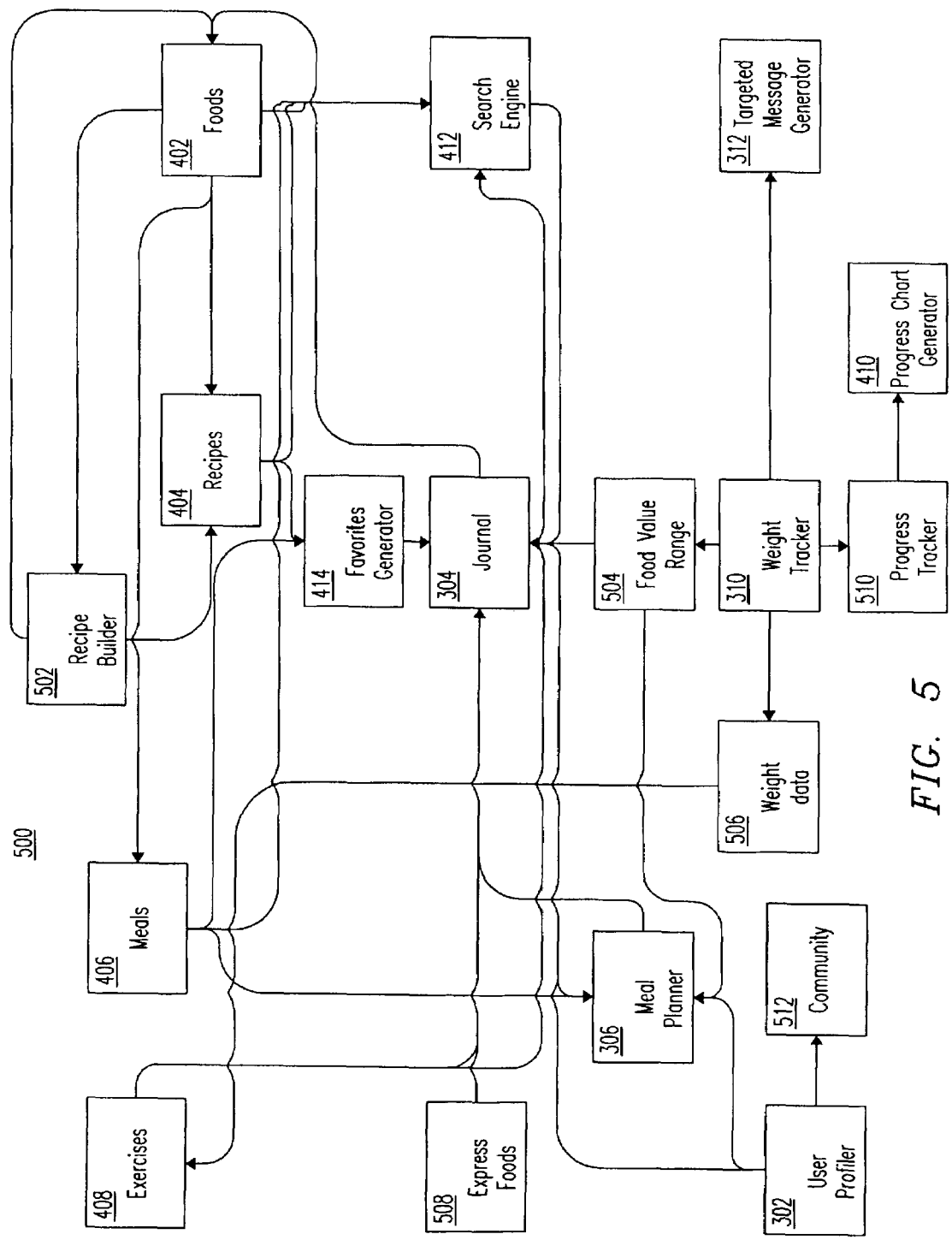
FIG. 5 is a more detailed exemplary block diagram of underlying architecture components of the weight control software system of FIG. 3, including the modules and tools, to illustrate the interoperability and interconnection within the interactive software environment and underlying architecture.

FIG. 5 is a detailed exemplary block diagram 500 illustrating such interoperability and interconnection. As shown, the journal 304 is centered among and interrelated with the other components of the weight control software system. While the block diagram 500 appears to be complex in the interrelationships between the components, it should be understood that this complexity is of the underlying architecture and not of the user interface. By having such a complex underlying architecture, the user interface and weight control program 115 (FIG. 1) are able to be simplified for operation thereof.

A number of additional components have been included in the block diagram 500 that were not present in FIGS. 3 and 4. These components include a recipe builder 502, rules database 504, express foods 508 and community module 512.

The recipe builder 502 is a tool that allows the user 110 to generate user-defined foods and recipes that may be stored in the foods database 403, entered into the journal 304, and saved in the favorites generator 414 for later use. Additionally, the recipe builder 502 may be utilized to share the recipe with others utilizing the weight control software system using, for example, public forums such as chat rooms, message boards, bulletin boards, or similar locations or activities where users 110 may communicate with one another (community). The recipe builder 502 provides the user 110 with an easy way to add and search for ingredients of a recipe. Once the ingredients are entered by the user 110, the recipe builder 502 is able to apply the general rules of the weight control program to provide the user 110 with information and guidance on what quantity of such food or meal is appropriate to accomplish the weight control goals of the user 110.

The rules database 504 is a database of the general rules for the weight control program 115. The representation of the rules database 504 in FIG. 5 as a separate "module" is for illustrative purposes only since such rules are expressed and manifested in the functionality of other, if not all, aspects of the weight control software system. FIG. 5 illustrates how the rules database 504 impacts and influences such tools and modules as the journal 304 and weight tracker 310.

The express foods 508 is a database that stores and maintains food information expressly defined by the user 110 in operating the weight control software system. If the user 110 cannot find a food by searching the food database 402, the express foods database 508 provides the user 110 with the means to input foods into the journal 0.304 and store such personal, customized foods.

Other components, such as a shopping list generator (not shown), may be integrated into the weight control software system to provide additional functionality to the system. In the case of a shopping list generator, the weight control program established for the user 110 may be utilized to determine the ingredients and generate a shopping list for the user 110 to print and/or electronically communicate to a grocery store or grocery delivery service. Accordingly, the added components are interoperable with existing components.

The following tools and modules of the weight control software system may be interoperable and interconnected, directly or indirectly, as generally set forth below:

The user profile 302 may be interconnected with the community module 512 so that the weight control software system may allow the user 110 to create a public profile that displays to other users 110 of the weight control software system certain personal information about such user 110.

The user profile 302 may interconnected with the meal planner 306 so that the weight control software system may provide the user 110 with customized meal plans according to, for example, the dietary preferences of the user 110 and the general rules of the weight control program 115 (FIG. 1).

The user profile 302 may be interconnected with the journal 304 so that the user 110 may customize the journal 304 according to his or her personal preferences and the general rules of the weight control program 115 (FIG. 1).

The weight tracker 310 may be interconnected with the progress chart generator 410 so that the weight control software system may provide the user 110 with a graphical chart illustrating the progress of the user 110 with respect to the weight control program 115 (FIG. 1).

The weight tracker 310 may be interconnected with the exercise database 408 so that the weight control software system may provide the user 110 with personal, customized exercises based on the weight of the user 110 and the general rules of the weight control program 115.

The weight tracker 310 may be interconnected with the targeted message generator 312 so that the weight control software system may provide the user 110 with instantaneous feedback in the form of targeted messages based on the updated weight of the user 110.

The weight tracker 310 may be interconnected with the rules database 504 so that the weight control software system may analyze the data entered into the weight tracker 310 in accordance with the general rules of the weight control program 115.

The rules database 504 may be interconnected with the meal planner 306 so that the weight control software system may provide the user 110 with customized meal plans according to weight of the user 110 and the general rules of the weight control program 115 (FIG. 1).

The rules database 504 may be interconnected with the journal 304 so that the journal 304 may operate and function within the general rules of the weight control program.

The exercises 408, foods 402, recipes 404, and meals 406 databases may be interconnected with the search engine 412 so that the weight control software system may provide the user 110 with search capabilities within the databases for exercises, foods, recipes and meals.

The search engine 412 may be interconnected with the journal 304 so that the user 110 may input and store search results obtained from databases with respect to exercises 408, foods 402, recipes 404 and meals 406 into the journal 304.

The foods database 402 may be interconnected with the journal 304 so that the user 110 may input and store foods in the journal 304 obtained from the foods database 402.

The express foods 508 may be interconnected with the journal 304 so that the user 110 may create, input and store personal, customized foods not found in the foods database 402 into the journal 304 and the favorites generator 414.

The favorites generator 414 may be interconnected with the journal 304 so that the user 110 may store as a favorite any exercises 408, foods 402, recipes 404, express foods 508, or meals 406 into the journal 304 for quick and simplified access when using the journal 304 in the future.

The foods database 402 may be interconnected with the recipe builder 502 so that the user 110 may create personal recipes using foods stored in the foods database 402.

The recipe builder 502 may be interconnected with the foods database 402 so that the user 110 may create personal, customized foods using the recipe builder 502 and store them in the foods database 402.

The favorites generator 414 may be interconnected with the recipe builder 502 so that the user 110 may store as a favorite any personal recipes created by the user 110 in the recipe builder 502 into the journal 304 for quick and simplified access when using the journal 304 in the future.

V. Detailed Descriptions of Certain Tool and Module Functionality

Profiler

In operation, with regard to FIG. 3, the user 110 initializes or establishes an account at 314 utilizing the user profiler 302. The user profiler 302 is operable to receive user information as shown in TABLE 1, which may include such criteria as weight, height, body fat, gender, and age, for example. Other criteria additionally may be utilized in generating a meal plan for the user 110 according to the general rules of the weight control program 115.

TABLE 1

Exemplary Initial Settings Provided by the User

Name
Gender
Weight
Height
Birthdate
Address
Phone Number
Profession

TABLE 1-continued

Exemplary Initial Settings Provided by the User

Marital Status
Other Characteristics (e.g., body type, personality)
Other Demographical Information (e.g., race, nationality)
Medical Information (e.g., pre-existing diseases)
Payment Information The profile data includes enough information to allow the weight control software system to establish settings in the journal 304 and develop the meal plan or list of meals for the user 110 with the meal planner 306 according to the general rules of the weight control program 115 (FIG. 1).

Referring now to FIG. 8, an exemplary graphical user interface (GUI) (e.g., web page) 800 is provided showing summary information for a personal profile of the user 110 and operated by the user profiler 302. The GUI 800 illustrates how the weight control software system collects personal information of the user 110. The personal profile information includes primary personal information 810, such as current weight, height, gender, and birthdate. Personal information, including name, address, phone number, e-mail address, profession, marital status, and identification number, may further be requested from the user 110 so as to provide the weight control software provider 105 (FIG. 1) general contact and related information. Other characteristics, such as attitude, athleticism, eye color, hair color, and weight goals may be requested of the user 110. The other characteristics may be useful in establishing a psychological profile to assist in the weight control efforts. Other demographic information 814 may include race, religion, ethnicity, and blood type, for example, so as to allow the weight control software provider 105 (FIG. 1), to be sensitive to the needs, customs, etc. of the user 110.

Determination of health restrictions 816 may also be of value to the weight control software provider 105 (FIG. 1). The health restrictions may include current diseases and existing or previous physical injuries. Such restrictions may include diabetes, cancer, mental illness, HIV, nursing mothers, and other health restrictions that may impact the application of the weight control program 115 (FIG. 1).

The weight control software provider 105 (FIG. 1) may further request a desired meal plan type 818. The desired meal plan types may include regular, higher-carbohydrate, higher-protein, and vegetarian. Each of these meal plan types has an associated percentage of carbohydrates, protein, fat, and fruits and vegetables that the user 110 is prescribed to eat in the daily food consumption regiment. TABLE 2 provides an exemplary food consumption daily regiment as prescribed by the desired meal plan types.

TABLE 2

Desired Meal Plan Types

| Type of Plan | Average Nutrient Mix Per Day | | | Servings per day |
| --- | --- | --- | --- | --- |
| | Carbs | Protein | Fat | Fruit and Veg |
| Regular | 55% | 20% | 25% | 5+ |
| Higher Carb. | 60% | 20% | 20% | 5+ |
| Higher Protein | 50% | 25% | 25% | 5+ |
| Vegetarian | 55% | 20% | 25% | 5+ |

Depending upon the weight-tracking day or other measurement day designated by the weight loss program, the user 110 may enter that day into the weight control software system. The weight-tracking day is utilized by the weight control software system to establish the first day of the week for the calendar of the user 110. Alternatively, the calendar may not be aligned with a weight-tracking day and the user 110 may or may not periodically perform a weight-tracking. If a weigh-in day is utilized, the journal may be calibrated such that the user 110 may more easily utilize the calendar.

Continuing with the discussion of FIG. 8, the weight control software provider 105 may further request payment information 822 so that an electronic payment may occur on a regular basis from the user 110 to the weight control software provider 105 (FIG. 1). The payment information 822 may include credit card information, debit card information, or other account information such that the electronic transaction may occur without further intervention by the user 110. A total subscription charge 824 may be calculated based on monthly charges for different services provided by the weight control software provider 105 for the users 110.

Upon completion of entering the initial personal profile, the weight control software system is able to set the food consumption parameters in the journal 304 and develop a meal plan via the meal planner 306 personalized for the user 110 as a function of the information provided in the personal profile. For example, the body mass index of the user 110 may be calculated based on the height and weight of the user 110.

In providing the user 110 with the ability to easily navigate the website, the site navigational elements 806 are utilized to allow the user 110 to rapidly access different topics on the website. The topics include home (i.e., home page of the user 110), the plan, community, success stories, food and recipes, healthy life, fitness, just for me, and shop. Each of these topics may provide the user 110 with information about the weight control program and the ability to manage personal data.

Within each web page selected from the site navigational elements 806, page navigational elements 808 are provided. The page navigational elements 808 may include journal, weight tracker, progress charts, my favorites, and assessment, for example, for "the plan" site navigational element. Other site navigational elements may have different page navigational elements 808. As shown, "the plan" is selected by the user and the personal profile is displayed on the website. A panic button 826 is provided on each page of the website to enable the user 110 to access "panic" type of information (see FIG. 22) in times of trouble or crises during the weight control process.

Journal

Referring again to FIG. 3, the journal 304 operates as a blank piece of virtual paper that the user 110 personalizes by recording food and exercise consumption in performing the personal data management, and enables the weight control software system to provide feedback as to when the user 110 is adhering to the weight control program 115 (FIG. 1). The journal 304 provides the user 110 with access to a calendar (not shown) that lists the meals and/or foods eaten for each present and/or past day. Meal plans generated by the meal planner 306 may also may be automatically and/or semi-automatically posted to the journal 304.

Referring again to FIG. 5, the user 110 may enter food and exercise into the journal 304 by searching the server databases 214 via the search engine 412. The search engine 412 allows the user 110 to search the server databases 214 for particular words and/or food metrics based on the general rules of the weight control program 115 (FIG. 1). The search engine 412 may be more comprehensive and allow the user 110 to search for types of foods, courses, or any other information that may be stored in the server databases 214 as understood in the art.

Any food or exercise entered into the journal 304 by the user 110 may be saved by the server databases 214 as a separate user-customized and defined "favorites" category. The favorites generator 414 allows the user 110 to identify and categorize individual foods, meals, recipes, and/or exercises that the user 110 often uses, thus allowing the user 110 to save time while utilizing the weight control software system.

Figure 9:
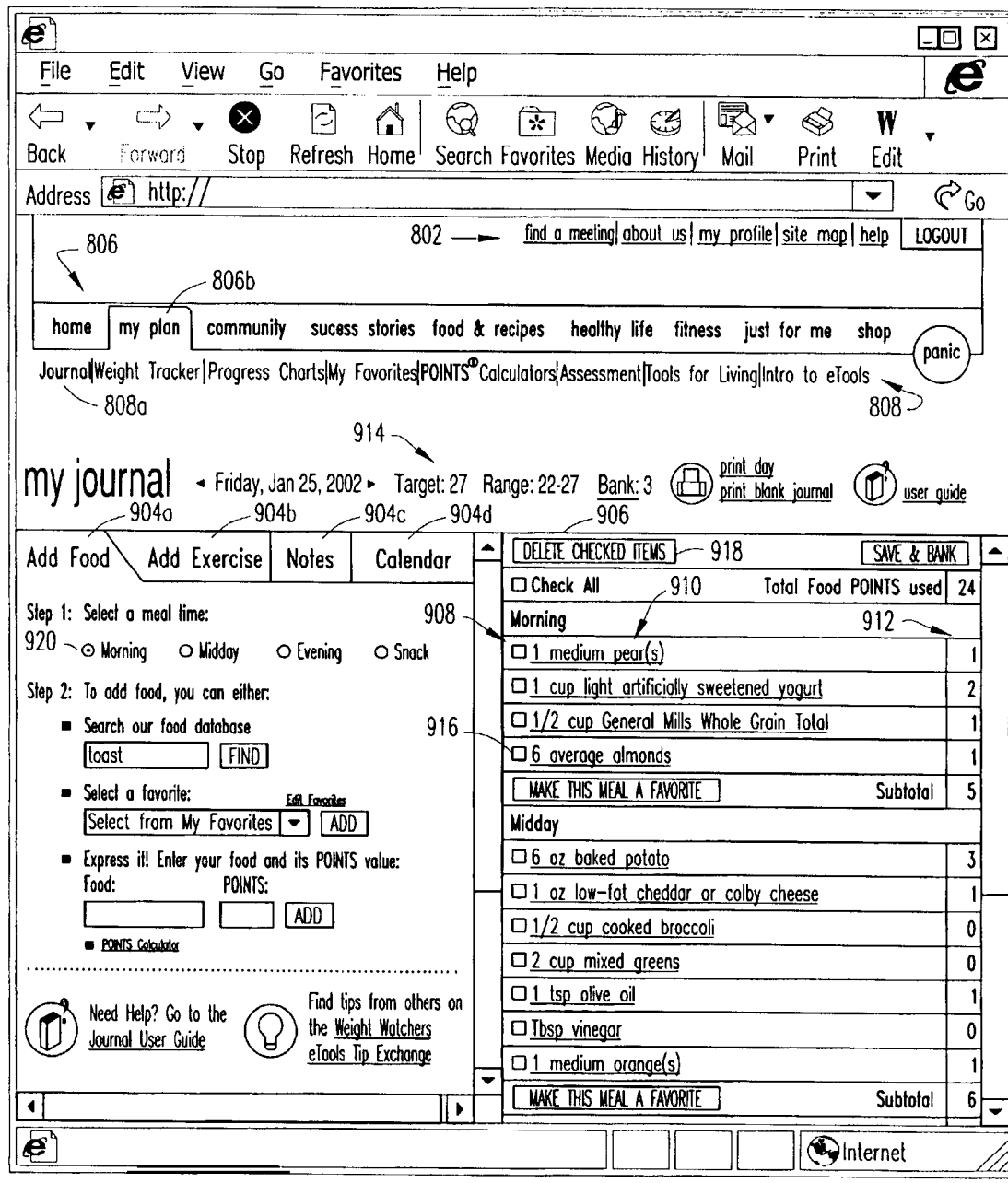
FIG. 9 is an exemplary web page of a journal illustrating the integration of foods from a food database into the journal consistent with the general rules of the weight control program of FIG. 1.

Referring now to FIG. 9, an exemplary web page 900*a* of the weight control software system operating the journal 304 on the computing system 125*b* is provided. As indicated, "my plan" 806*b* of the site navigational elements 806 is selected. Additionally, the "Journal" 808*a* of the page navigational elements 808 is selected. Again, the journal 304 allows the user 110 to post and record consumed foods in a calendar format established in conjunction with the weight control program 115 supported by the weight control software system. And, the meals and/or foods consumed by the user 110 may be stored by the journal 304 for future reference purposes by the user 110 or weight control software system.

Four functional elements 904*a*-904*d* (collectively 904) may be selected in working with the journal 304. A food consumption section 906 presents meals for each part of the day. For example, the morning portion 908 shows a meal having one medium pear, one cup of artificially sweetened yogurt, one-half cup of General Mills Whole Grain Total.™., and six average almonds. Each food item 910 has an associated food value 912 as determined by the general rules of the illustrated weight control program 115, for example. However, foods may be categorized in any other way, such as calories or grades, based on the general rules of the weight control program 115 (FIG. 1). In one embodiment, the food values may be determined and tallied in terms of "POINTS" as specified by a particular weight control program 115. POINTS is a registered trademark of Weight Watchers International, Inc. See, U.S. Pat. Nos. 6,040,531 and 6,436,036 to Miller-Kovach et al. for further discussion of POINTS. A subtotal and daily total for each meal is provided in the food consumption section 906. The user 110 is able to tailor the foods for the day by selecting and unselecting food items 910 in the food consumption section 906 based on the general rules of the weight control program 115.

To alter the food items 910, the user 110 may add and delete food items. For example, the user 110 may delete the six average almonds by selecting a check box 916 associated with the six average almonds. A "delete checked items" soft-button 918 may be selected to delete the food items having checked boxes 116 selected.

Continuing with FIG. 4, to add a food item, the "Add Food" functional element 904*a* may be selected. The user 110 may then select via soft-radio buttons 920, a meal time for which to add food. The user 110 may then perform a search of the foods database 402, select a favorite meal, or add a food item via an "express" data entry technique. Once a food is selected or entered, the user 110 may add the food to the food consumption section 906 by selecting an "add" soft-button. The food is then automatically placed into the food consumption section 906.

The journal 304 is highly interoperable with other functions and features of the weight control software system. As shown, the site informational elements 802, site navigational elements 806, and page navigational elements 808 are available for the user 110 to select for rapid movement within the website. Upon selecting one of the elements 802, 806, or 808, the information entered into the journal 304 is instantly accessible at other locations within the website. Again, this interoperability and interconnection between the elements is provided by way of the underlying architecture of the components in FIG. 5.

Figure 11:
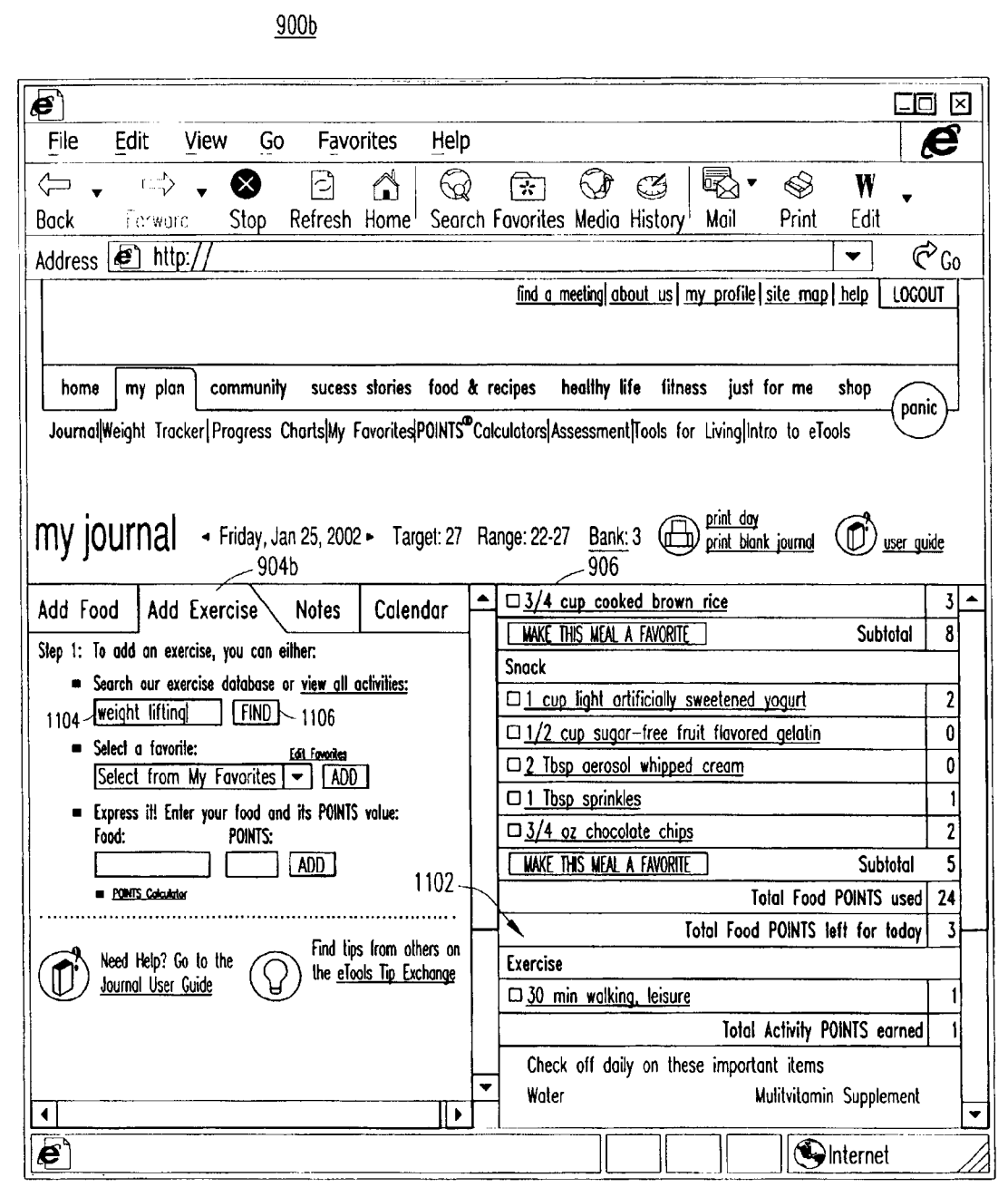

FIG. 11 is another exemplary web page 900b of the journal of FIG. 9. The "Add Exercise" functional element 904b is selected so as to provide the user 110 with the ability to add exercises to an exercise section 1102 of the food consumption section 906. As shown, the exercise section 1102 includes one established exercise (i.e., "thirty min walking, leisure"). Generally, weight control software system functions so that exercise is used to offset food consumed so as to factor into the total amount of recommended food that the user 110 may consume in a given day. However, it should be understood that other general rules that factor into the total amount of recommended food provided by the weight control program 115 (FIG. 1) may be integrated into the weight control software system.

Other exercises may be added to the exercise section 1102 by searching the exercise database 408, searching the favorites from the favorites generator 414, or adding a personal, customized exercise. As shown, the term "weight lifting" may be entered into a search text box 1104. Upon selecting a "find" soft-button 1106, the user 110 may find and select a weight lifting exercise and add it to the exercise section 1102. By adding exercises, the user 110 may have control and flexibility over the weight control program 115 (FIG. 1) as established by the weight control software system.

Figure 12:
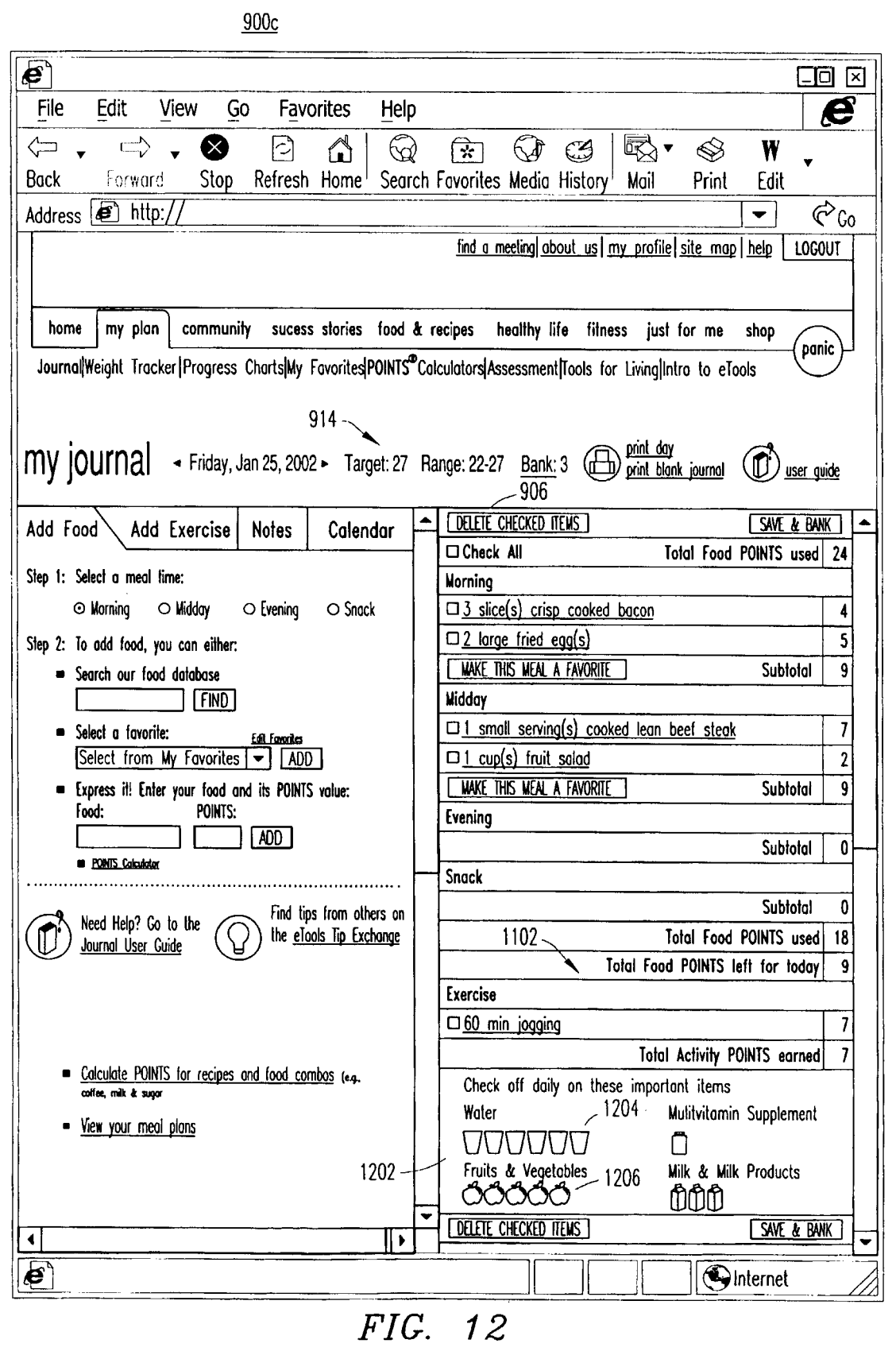

FIG. 12 is yet another exemplary web page 900c of the journal 304 of FIG. 9. The food consumption section 906 illustrates the flexibility of the journal 304 according to the principles of the present invention. As shown, only portions of two meals (i.e., morning and midday) have been established by the user 110 via the meal planner 306 or by entering the foods in manually. As shown, the morning meal currently includes bacon and eggs, and the midday meal includes beef steak and fruit salad. As is understood by the user 110 of the weight control software system, liquids, such as orange juice and soda, may further be added to the morning and midday meals. The evening meal has yet to be established, but may easily be entered by searching the database, selecting a favorite food and/or meal, and/or expressing a food based on the general rules of the weight control program 115, so as to be entered into the food consumption section 906. Accordingly, the foods may be entered and tallied to notify the user 110 whether the amount of food consumed is within the recommended consumption range 914 according to the general rules of the weight control program 115 (FIG. 1). In one embodiment, the recommended consumption range 914 may be a function of calories. Alternatively and/or additionally, the recommended consumption range 914 may be a function of fat and fiber. Upon the food and exercises being consumed and performed, respectively, the journal 304 stores the items for future review.

A suggested food items section 1202 is provided beneath the food consumption section 906 and exercise section 1102 to provide for a balanced diet. The suggested food items section 1202 is generally consistent with the desired meal plan type 818 selected by the user 110 in the personal profile 302 and the general rules of the weight control program 115 (FIG. 1). To select a particular suggested food item, icons, such as water cups 1204, tomatoes 1206 (representing fruits and vegetables), multi-vitamins and milk cartons (representing dairy products) are provided. As the user 110 consumes the food items, the user 110 records consumption by selectively "clicking" on the associated icon.

Figure 13:
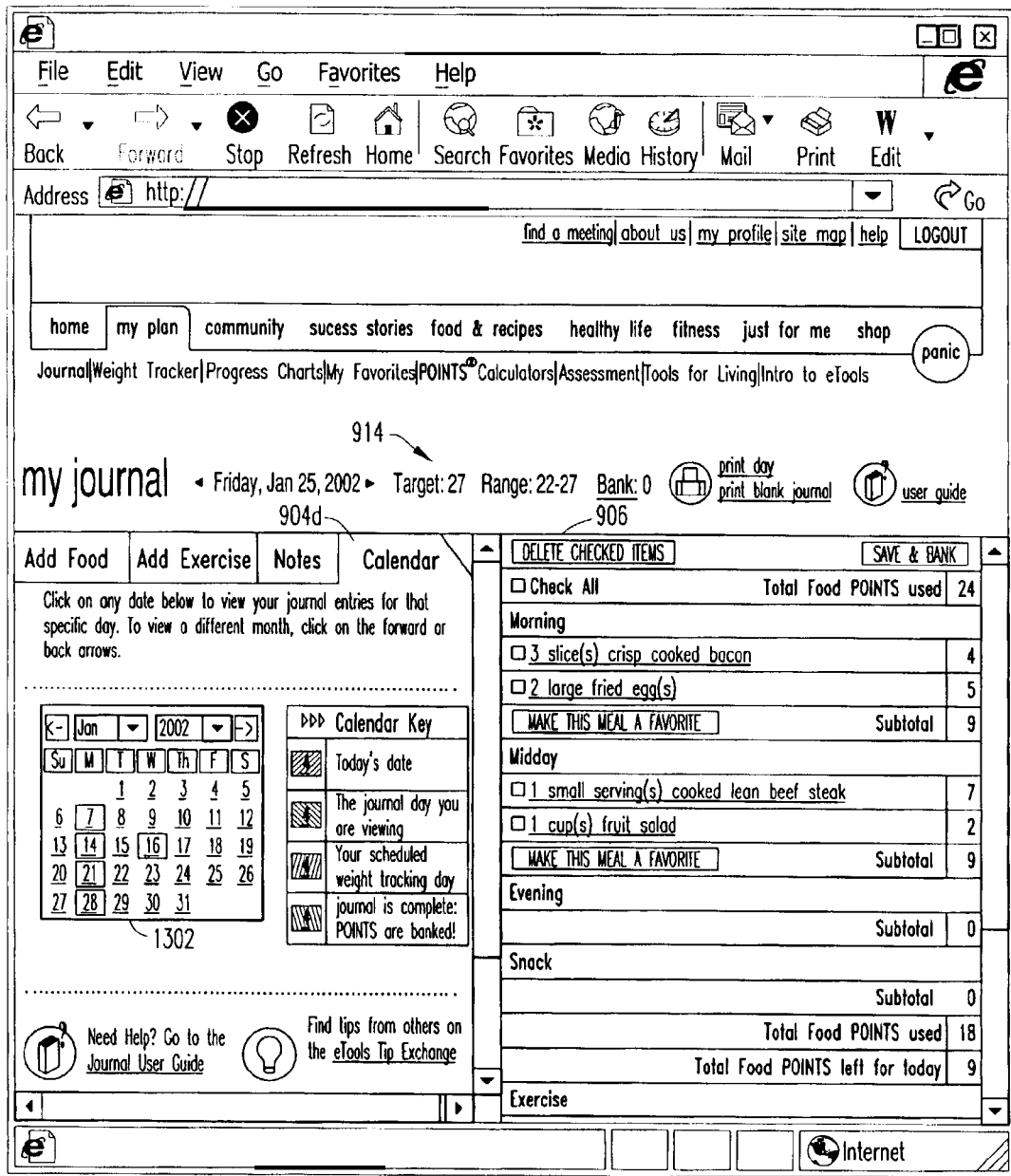
FIG. 13 is another exemplary web page view of the journal of FIG. 9 illustrating additional functionality in accordance with the principles of the present invention, including the integration of a searchable monthly calendar.

FIG. 13 is yet another exemplary web page 900d of the journal 304 of FIG. 9. This view shows that the "Calendar" functional element 904d is selected. As shown, a calendar 1302 is provided for the user 110 to select individual days of a month. In this case, Jan. 16, 2002 has been selected. The foods for the day are shown in the food consumption section 906 so that the user 110 may follow and/or alter the foods as desired. Accordingly, an alterable meal plan schedule or time-based plan is generated by the foods being selected in advance for the user 110 to consume.

Figure 16A:
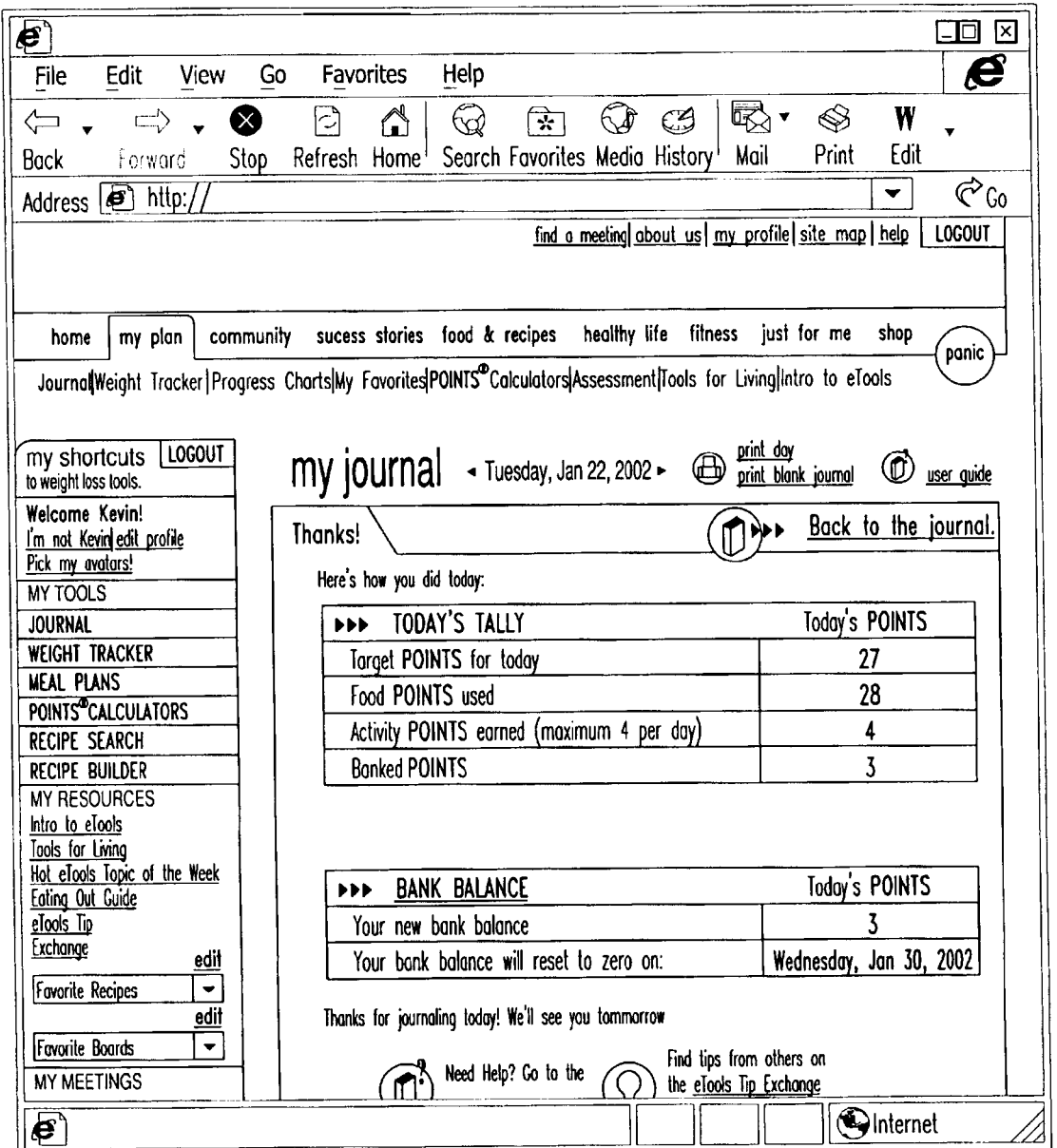
FIGS. 16A and 16B are other exemplary web pages of the journal of FIG. 9 illustrating the ability of the journal to evaluate, manage and display consumption goals and valuations for any food and exercise entered into the journal by the user according to the general rules of the weight control program of FIG. 1.

FIG. 16A depicts an exemplary web page 900e of the journal 304 of FIG. 9 providing a tally for an individual day of the food and exercise for the user 110. As shown by example, the illustrated weight control program 115 (FIG. 1) has assigned a recommended food consumption target of twenty-seven (27). Based on the general rules of the weight control program 115 (FIG. 1), the user 110 has consumed an amount of food (based on quantity and food type) equal to 28 and has exercised (based on type and duration) in an amount equal to four (4). The general rules of the illustrative weight control program 115 (FIG. 1) also allow the user 110 to consume an additional amount of food equal to three (3) that the user 110 was permitted but did not eat on a prior day. The additional amount of food for consumption is computed in the following manner: 28 food values of consumption minus 4 activity values=24, so that 27 target values minus 24=3 additional food values available for consumption. It should be understood that the general rules are established by the weight control program 115, and that other rules may be utilized to produce or enhance the same or similar functionality for providing a weight control program 115 for the user 110.

Figure 16B:
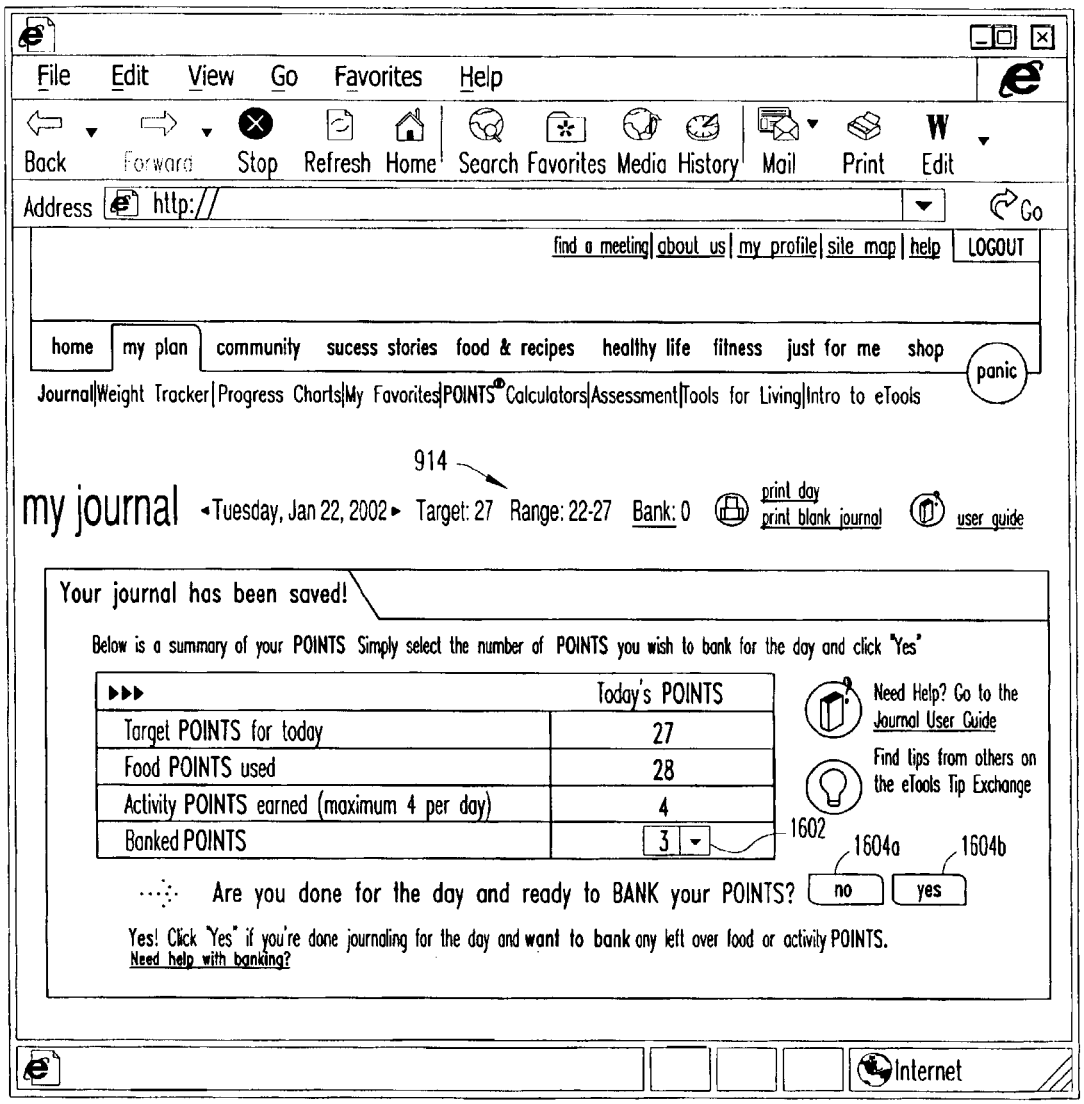

FIG. 16B is another exemplary webpage 900f of the journal of FIG. 9 providing the user 110 with the ability to accept the tally of food and activity values. As shown, the tally shows that the value for the available amount of food to consume is three (3) and a selection tool (i.e., pull-down menu) 1602 is available to alter that value by the user 110. Once the user 110 is ready to store the selected value, up to a maximum value established by the tally for the day, the user 110 may select a soft-button 1604a or 1604b to reject or accept the selected value. Upon the user 110 selecting soft-button 1604b indicating that the user is ready to store a value of three (3), the webpage 900f is updated such that the banked value may be shown in the meal plan points information 914 (see FIG. 16A).

Meal Planner

In addition to individual foods, recipes and exercises, the user 110 may access through the meal planner 306 certain predetermined meal plans developed in accordance with the general rules of the weight control program and stored on the server databases 214. The meal planner 306 determines meals for each user 110 in accordance with the personal profile of the user 110 and the general rules of any weight control program 115.

If the user 110 does not want to use a meal provided by the meal planner 306, the user 110 may replace this meal with an alternative meal generated by the meal planner 306 and consistent with the general rules of the weight control program 115. The user 110 may input any meal generated by the meal planner 306 into the journal 304 and save the meal in the favorites category of the user 110. Furthermore, as the weight tracker 310 is updated by the updated weight 322 as input by the user 110, the meal planner 306 automatically alters the dietary recommendations of the weight control program 115 (FIG. 1) based on the updated weight 322 in accordance with the general rules of the weight control program 115. By altering the dietary recommendations of the weight control program 115, the recommended quantity and type of food is altered such that both the journal 304 settings and the meals provided to the user 110 via the meal planner 306 are automatically updated.

As discussed in detail with regard to FIG. 10 hereinafter, there are generally two types of weight control users 110, (i) structured and (ii) non-structured users. The structured users typically want to know specific meals to eat that follow the general rules of the weight control program 115. To provide for the structured users, the meal planner 306 predetermines the meals for the user 110 that meet the rules of the weight control program 115. The journal 304 allows the user 110 to enter the meals generated by the meal planner 306 and consumed by the user 110 as a daily record. Accordingly, the meal planner 306 is coupled to the journal 304. The user 110 may alter the planned meals by substituting the planned meals with other meals suggested by the meal planner 306. By allowing the user 110 to choose between creating a customized meal by selecting and entering foods into the journal 304 or selecting a meal created by the meal planner 306, the weight control software system may accommodate both structured and non-structured user types.

Figure 10:
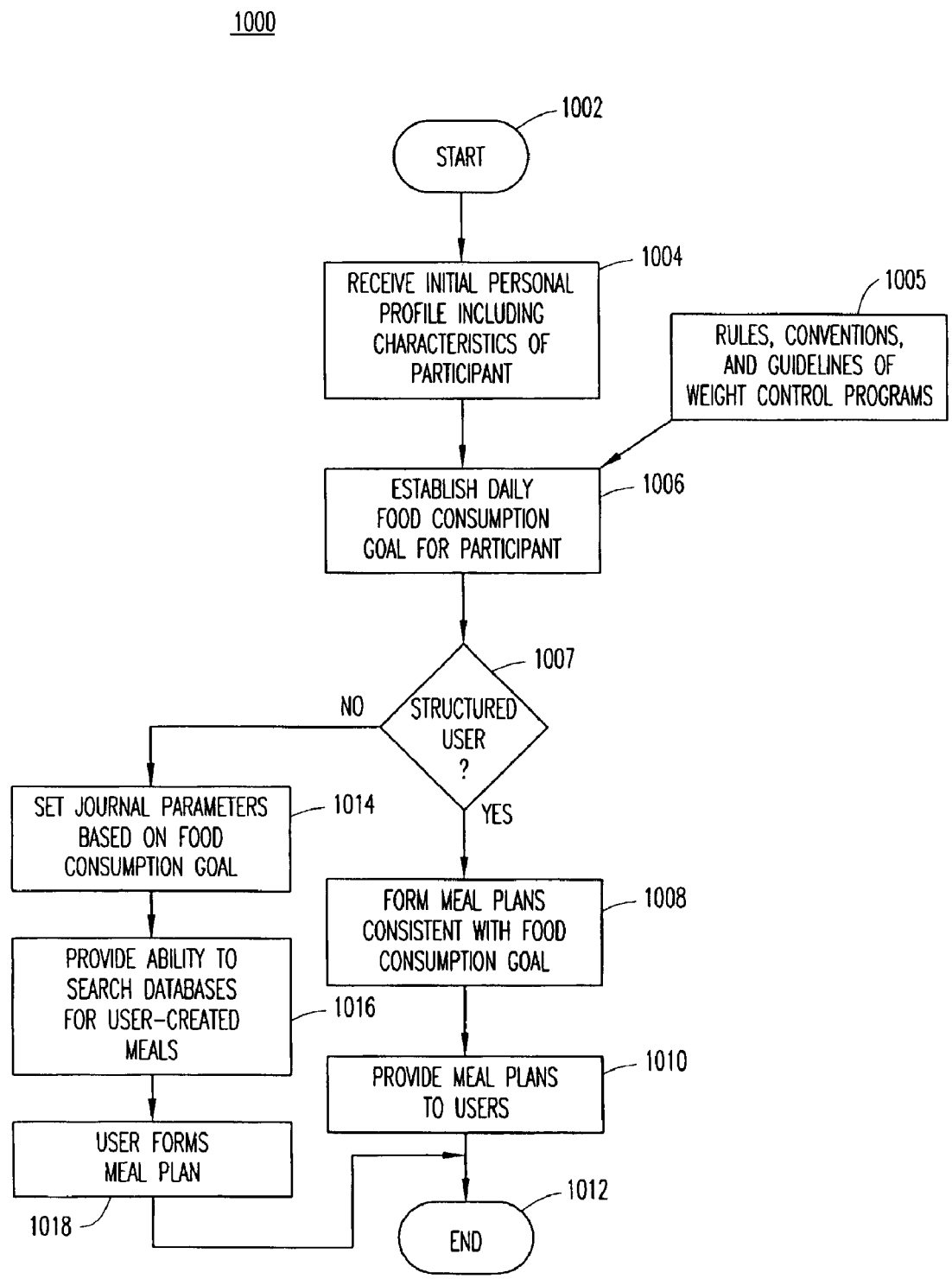
FIG. 10 is an exemplary flow diagram illustrating the customization of the parameters of the journal of FIG. 9 and meal plans of FIGS. 14 and 15 provided by the weight control software system based on a profile and food consumption goal for a user established by the general rules of the weight control program of FIG. 1.
Figure 14:
FIG. 14 is an exemplary web page of a multiple-day meal plan generated by a meal planner module of FIG. 5 and consistent with the general rules of the weight control program of FIG. 1.

FIG. 10 is an exemplary flow diagram 1000 illustrating the customization of the parameters of the journal of FIG. 9 and meal plans of FIGS. 14 and 15 provided by the weight control software system based on a profile and food consumption goal of a user established by the general rules of the weight control program of FIG. 1. The process starts at step 1002. At step 1004, an initial personal profile including characteristics of a user 110 is received. At step 1005, rules, conventions and guidelines of the weight control program 115 are applied or established by the weight control software system. A daily food consumption goal for the user 110, which is based on the personal information of the user 110 and the general rules of the weight control program 115, is established at step 1006.

At step 1007, a determination may be made as to whether the user 110 is a structured or unstructured user 110. In other words, it is determined whether the user 110 wants a meal plan automatically created or the user 110 wants to create the meal plan. The determination may be made by the user selecting a control element, such as a soft-button, or by inspecting the profile of the user 110.

If it is determined that the user 110 is a structured user, then at step 1008, the weight control software system sets parameters in the journal 304 and creates meals (i.e., a list of meals or meal plan) generated by the meal planner 306, in each case, in accordance with the personal information of the user 110 and the general rules of the weight control program 115. At step 1010, the meal plan is provided to the user 110. The process ends at step 1012.

If it is determined that the user 110 is not a structured user, then at step 1014, journal parameters are set based on the food consumption goal as determined by the weight control software system based on the weight control program 115. At step 1016, the weight control software system provides the user with the ability to search databases for user-created meals. At step 1018, the user 110 may form the meal plan by (i) searching the food database 402, favorites generator 414, or entering express foods 508, (ii) a meal generated by the meal planner 306, or (iii) a combination of both. The user 110 may enter the meals into the journal 304. The process ends at step 1012.

FIG. 14 is an exemplary seven day meal plan 1400 provided on a web page as generated by the meal planner 306 of the weight control software system and consistent with the general rules of the weight control program 115. As shown, "food and recipes" site navigational element 806e is selected to provide the user 110 with the food and recipe portion of the website. Additionally, the "Meal Plans" page navigational elements 808c is selected such that the seven day meal plan is provided to the user 110. The seven day meal plan begins on Wednesday, which may correspond to the weight-tracking day established by the user 110 in the initial profile of the user 110 as entered in the GUI 800.

The seven day meal plan 1400 may include both the names of meals and any classification associated with meals based on the general rules of the weight control program 115. For example, on Wednesday, the morning meal is "cheese omelet", midday meal is a "veggie chili", evening meal is an "apricot turkey breast", and snack is "snacks and treats". The cheese omelet has been deselected by the user selecting or clicking on the check box 1402 utilizing the input control device 230b. The deselection indicates that the user 110 has not consumed the cheese omelet so that the cheese omelet is not posted to the journal 304.

In the web page of the seven day meal plan 1400, a tools section 1404 is provided to allow the user 110 to select soft-buttons associated with a number of tools, including journal, weight tracker, meal plans, food calculator, recipe search, and recipe builder. These tools provide interoperability with the web page of the meal planner 306. In other words, tools other than the one being utilized may be selected via soft-buttons and the functional operation of one tool may affect the information to be utilized by another tool. It should be understood that the tools section 1404 includes an exemplary list of tools and that others or alternatives may be included.

FIG. 15A is an exemplary web page 1500a showing a single day of the seven day meal plan 1400 of FIG. 14. The single day may be selected by selecting a hyperlink (e.g., Wednesday) on the seven day meal plan 1400. As shown, each of the meals, including morning, midday, evening, and snack, are provided for the user to select and deselect to enable automatic posting to the journal 304. A pull-down menu tool 1502 as understood in the art is provided for the user 110 to swap the present morning meal for a different meal. Swapping of the meal is relatively straightforward as the weight control software system is interactive and interoperable. In other words, in swapping a meal, another web page may be generated that allows the user 110 to link with the server databases 214 and to select a different meal to replace an existing one.

Upon updating the meal plan, the user 110 may select a soft-button 1504 to update the meal plan. Accordingly, upon the meal plan being updated, each other page of the weight control software system includes access to the information that has been updated.

Again, as discussed with respect to FIG. 7, to provide the user with a faster interface, the data updated during the course of a session (i.e., while the user is logged onto the weight control software system) is maintained, thereby not requiring the computing system 125b to communicate over the network 216 with the server 202 during the session. Upon the user logging off of the weight control software system, the data updated during the session may be uploaded to the server 202 to be stored in the server databases 214 on the storage device 212.

Figure 15B:
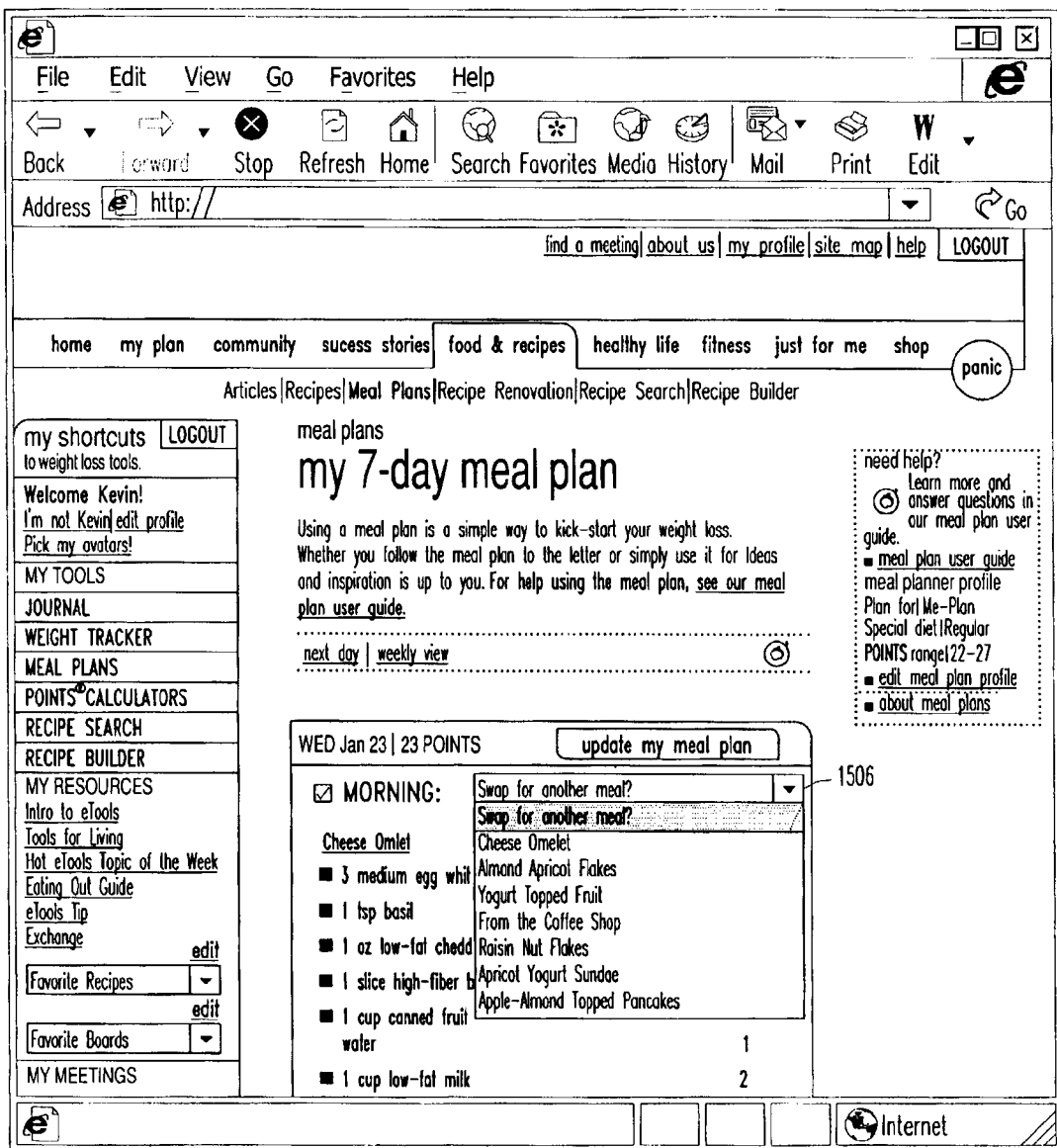
FIG. 15B is an exemplary web page illustrating the ability of the user to replace meals of FIG. 15A with alternative meals generated by the meal planner module of FIG. 5 and consistent with the general rules of the weight control program of FIG. 1.

FIG. 15B is a page 1500b that provides the ability for the user 110 to swap meals provided in the web page of FIG. 15A. As shown, the user 110 has selected the morning meal (i.e., cheese omelet) to swap. A pull-down menu element 1506 provides the user 110 with a variety of meals to select from in order to replace the morning meal. The user 110 may simply highlight one of the meals, such as "Yogurt Topped Fruit", and the morning meal is swapped.

Weight Tracker

The weight tracker 310 utilizes the general rules of the weight control program 115 to maintain the information of the user 110. The weight tracker 310 is operable to automatically alter the recommended amount or type of food a user 110 should consume based on the updated weight 322 into the weight tracker 310 and the general rules of the weight control program 115. In addition, the meals provided to the user 110 via the meal planner 306 are automatically altered. The user profiler 302 may also be updated with the updated weight 322.

As the user 110 loses weight, the weight tracker 310 may reduce the amount or type of food that the user 110 is recommended to consume because as the user 110 loses weight, fewer nutrients are required by the user 110. The recommendation may be based on a body mass index (BMI), cholesterol levels, body fat measurements, etc., and lowered using a linear or non-linear technique. It should be understood that the weight control program 115 may additionally be utilized to assist a user 110 in gaining weight. In the case of gaining weight, the recommended amount or type of food may be set higher such that the weight control program 115 operates to increase the body mass index of the user 110.

Figure 21:
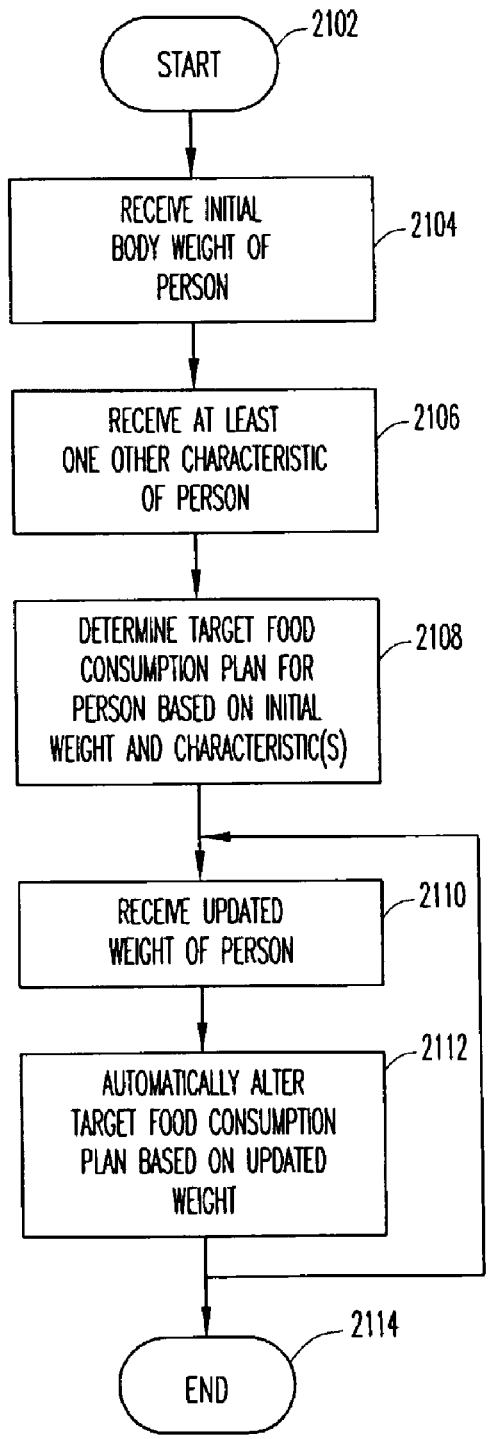
FIG. 21 is an exemplary flow diagram for utilizing updated weight entered into the weight control software system of FIGS. 2-5 by the user to adjust the consumption goals, meal plans or any other aspect of the weight control software system according to the general rules of the weight control program of FIG. 1.

FIG. 21 is an exemplary flow diagram for utilizing the updated weight 322 and adjusting the weight control software system consistent with the weight control program 115. The process starts at step 2102. At step 2104, initial body weight of the person (i.e., user 110) is received. At step 2106, at least one other characteristic of the person is received. A target food consumption plan is determined for the person based on the initial weight and characteristics of the person. The target food consumption plan may be a predetermined amount of food to consume based on food values associated with food items, where the food values may be a function of ingredients and/or nutritional value (e.g., fat, calories, and fiber). After establishment of the target food consumption plan, the updated weight 322 of the user 110 is received by the weight tracker 310 at step 2110. Based on the updated weight 322 of the user 110, the target food consumption plan is automatically altered at step 2112.

The automatic altering of the target food consumption plan is based on the rules of the weight control program 115 and may be utilized to adjust the recommended amount or type of food for a particular day, which ultimately alters the target food consumption plan for any particular day based on such recommendation. By automatically altering the target food consumption plan, the user 110 may simply focus on adhering to the weight control program 115. The process repeats steps 2110 and 2112 until the user 110 ultimately foregoes the weight control program 115, if ever, where the process ends at step 2114.

The general rules of the weight control program 115 may range from simple to complex and may be based on any number of criteria, such as food items, calories, nutrients, weight measurements, and exercise levels. In one embodiment, the rules of the weight control program 115 prescribe that the user 110 is to lose not more than a maximum number of pounds over a certain amount of time. As understood in the art, by maintaining a steady loss of weight, the user 110 is provided a safe way to lose weight. Other rules may be applied for safety or medical reasons as established for a specific user based on the profile or otherwise.

FIG. 19 is exemplary web page for providing weight tracking capability using the weight tracker 310. As the user 110 continues on with following the weight control program 115 provided by the weight control software system, the user 110 may continue to follow a more regimented version of the weight control program 115. Body weight of the user 110 may be measured on a periodic or aperiodic basis and enter the updated weight 322 using the weight tracker 310 function by selecting "Weight Tracker" page navigational element 808b under the "my plan" site navigational element 806b. After the updated weight 322 is entered, it is shown in the current information section 1902 to provide feedback to the user 110. As shown, the weight tracker 310 is interoperable with other elements and functions of the weight control software system. Accordingly, as shown and discussed with regard to FIG. 3, the weight tracker 310 is utilized to receive user input (i.e., updated weight 322) and that the weight control software system may adjust the user profile 302 and meal plan accordingly as the weight of the changes.

Upon or after entry of the updated weight 322, a targeted message may be delivered by the targeted message generator 312 in an instantaneous or real-time, or substantially real-time fashion such that the user 110 is provided feedback based on the updated weight 322. The feedback in the form of the targeted message may be instantaneous. Alternatively the targeted message may be delayed. The targeted message generator 312 may issue an instant message, e-mail, and/or customized web page, for example. The targeted message may include a congratulatory statement, encouragement statement, motivational statement, or other statement or content made to the user 110 based on the updated weight 322. In other words, if the user 110 loses weight from the previous week, then the targeted message generator 312 may congratulate the user on his or her accomplishment.

Since the loss of a few pounds for one individual may be relatively insignificant relative to his or her ultimate weight goal, the targeted message may be adjusted based on the goals set by the user 110. By providing instantaneous feedback to the user 110, instant gratification or satisfaction may be provided to the user 110 to help encourage and motivate the user 110 to maintain use of the weight control program 115 and use the weight control software system. The targeted message may also provide a warning if the user is losing weight too quickly. In addition, the targeted message may be tailored to the perceived success or failure of the user 110 with his or her weight loss by asking the user 110 questions about his or her weight loss or gain prior to delivering the targeted message. The targeted message may be just what the user 110 needs to provide that added recognition to maintain a healthy attitude on the journey to his or her ultimate weight goal.

Recipe Search

Figure 17:
FIG. 17 is an exemplary web page illustrating the ability of the user to search for recipes according to food type, any food valuation established by the general rules of any weight control program or any other criteria and automatically place selected recipes directly into the journal of FIG. 9.

FIG. 17 is an exemplary web page 1700 for providing the user 110 with the ability to search for recipes. As shown, the user 110 is provided with search information entry elements 1702 for performing a keyword search within certain parameters consistent with the rules of the weight control program 115. As shown, an exemplary search for keyword "chicken"

within the parameters of 5 to 7 (based on the general rules of the illustrative weight control program 115) has been performed. Any recipe that has the term chicken and is within a range of 5 to 7 is provided by the weight control software system for the user 110 to view. Additionally, an indication as to which course and how much time the recipe takes to prepare is provided. These recipes may be selected and entered into the journal 304 or saved as favorites as provided by the weight control software system. It should be understood that the recipes that may be searched are found in the server databases 214, where the recipes include pre-established recipes from the weight control program 115 or recipes of the user 110. Additionally, the search may include a recipe listing from a community database that includes recipes from other users 110.

Recipe Builder

Figure 18:
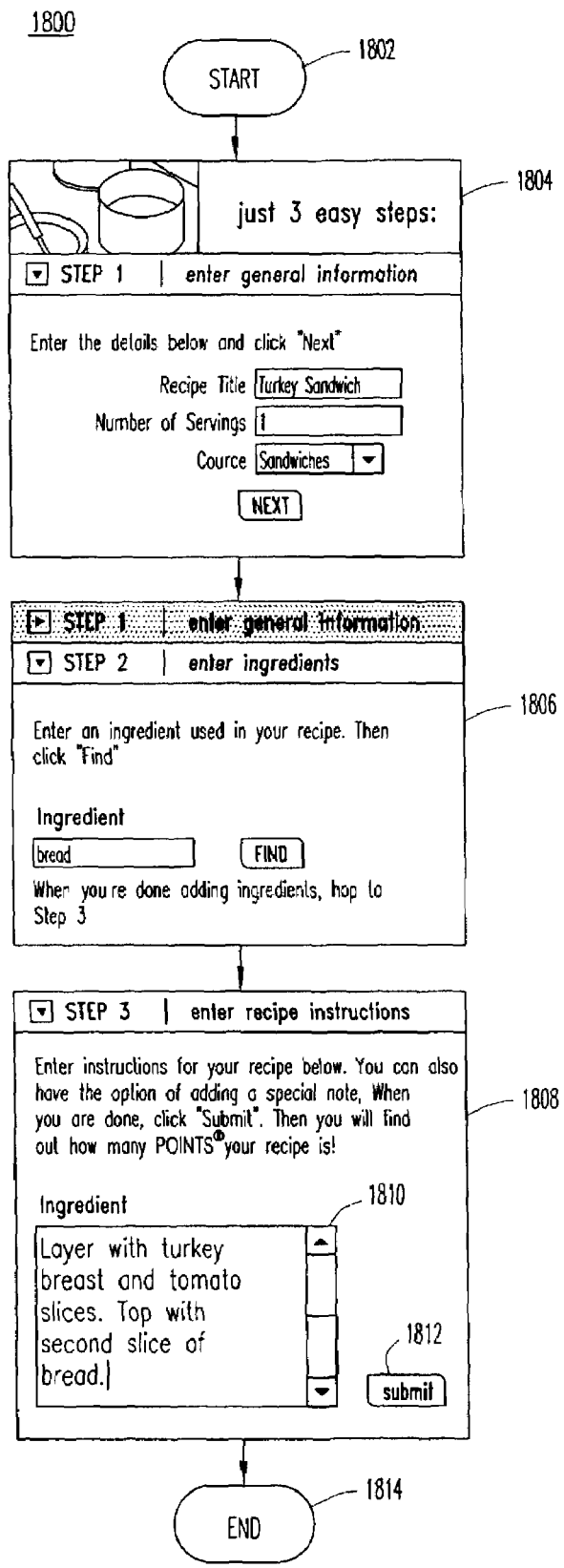
FIG. 18 is an exemplary set of instructions for using the recipe builder of FIG. 5 to input and store recipes of the users and share such recipes with other users of the weight control software system of FIGS. 2-5.

FIG. 18 is an exemplary set of instructions 1800 for using the recipe builder 502 to generate recipes as preferred by the user 110. The recipe builder 502 allows the user 110 to create recipes using food items that may be found in the food database 402 or items entered manually by the user 110. As shown, there are three primary steps to building a recipe. The process starts at step 1802. At step 1804, the user 110 enters a recipe title, number of servings, and course to which the recipe applies. At step 1806, individual ingredients of the recipe are entered. To add the individual ingredients, a text field is provided for the user 110 to enter an ingredient. The ingredient may be general, such as "bread", and a search may be performed for any ingredient including the term "bread" or other substantially related term. Upon finding a particular bread ingredient, such as whole, wheat, or white, the user may select the ingredient and continue adding ingredients for the recipe.

At the end of entering the ingredients for the recipe, recipe instructions may be entered at step 1808. The recipe instructions may be entered into a text box 1810 so that the user 110 or others users of the weight control software system may follow the instructions for preparing the recipe. The recipe may be submitted by selecting a soft-button 1812. Upon submission, the recipe database 404 may be updated on the user computing system 125b and, upon logging out of the weight control software system, updated on the server 202. The process ends at step 1814. The recipe may thereafter be edited, deleted, or searched for using other elements within the weight control software system.

Progress Charts

The weight tracker 310 updates the progress chart generator 410 to monitor parameters and/or performance indicators that are indicative of the progress of the user 110 in following the weight control program 115. For example, the progress chart generator 410 may receive updated weights 322 from the weight tracker 310 and display the updated weights over a period of time so that the user 110 can monitor weight loss or gain, for example. By graphically monitoring or feeding-back weight loss progress, the user 110 may be additionally motivated. The graphical representation may additionally allow the user 110 to identify successful weeks of weight loss so that the user 110 may review the journal 304 to determine what meals made those weeks successful.

Figure 20:
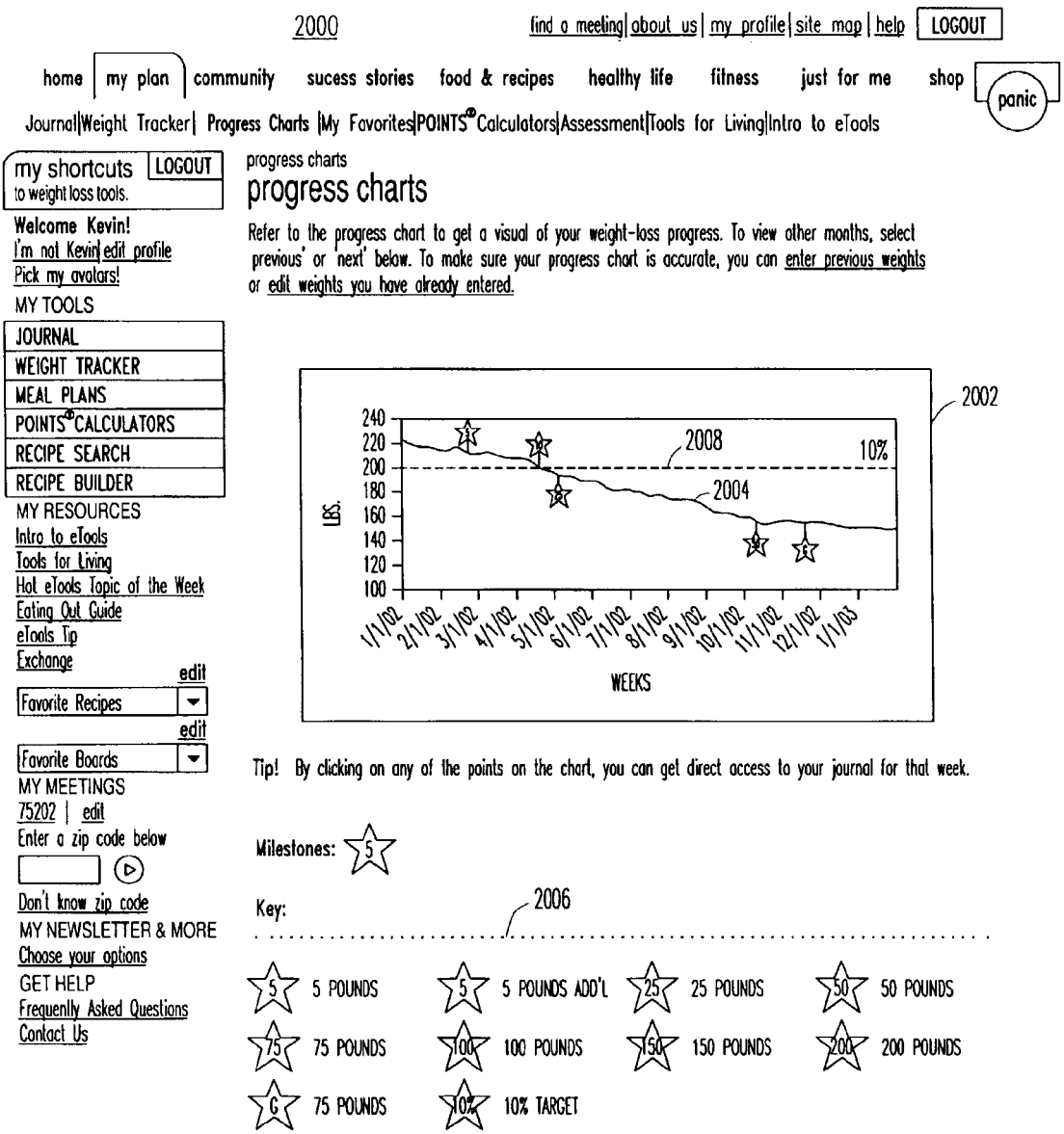
FIG. 20 is an exemplary web page of the weight tracker of FIG. 19 illustrating the ability of the weight control software system to generate a progress chart and integrate and interconnect the progress chart with specific days of the journal of FIG. 9.

FIG. 20 is an exemplary web page 2000 providing a progress chart 2002 that is generated by the weight tracker 310. The progress chart 2002 is a line graph that shows weight per date. Each week or the period that the user 110 weighs in, the user 110 enters the weight into the weight tracker 310. The weight may thereafter be applied to the progress chart 2002 and shown as a point on the line 2004.

A number of targets or milestones may be applied to the line 2004, such as a 5, 10, 25, and 50 pound point as indicated by the stars shown on the progress chart 2002 and identified in the key section 2006. Once the user 110 reaches the goal weight, a star with a "G" is placed on the chart 2002. Additionally, a 10 percent dashed line 2008 is shown on the chart 2002. It should be understood that other milestones and indicators may be utilized, consistent with the rules of the weight control program 115, to provide information to the user 110 to aid and encourage the user 110 to maintain the weight control process. Again, such feedback tools provide the user 110 with gratification and satisfaction in the overall weight control process. If the user 110 sees a week of successful weight control, then the user 110 may select the week via the input control device 230b and associated soft-button or indicia and have the journal 304 display the selected week.

Panic Button

Figure 22:
FIG. 22 is an exemplary web page illustrating a panic button, whereby a user in need of immediate motivation can access a list of titles operating as hyperlinks to motivational information about the weight control program of FIG. 1.

FIG. 22 is an exemplary web page 2200 providing a list of titles operating as hyperlinks to information, where the web page 2200 is accessed by selecting a "panic" button 826 of FIG. 8. If during the course of the user 110 being on the weight control program 115, the user 110 finds him or herself becoming worried, upset, or panicky, the user 110 is provided with the panic button 826 on each of the web pages as provided herein. The user 110 may select the panic button 826 to engage the web page 2200.

On the web page 2200, a number of different selectable items, which may be titles or other indicators that the user 110 may feel is appropriate or related to his or her current feelings, are listed. For example, such titles may include "I Gained This Week" or "None of My Jeans Fit Me Anymore!", which indicate the type of encouragement, story, motivation, or other words of advice that are provided by the weight control software provider 105. By having this online emotional support, the users 110 may tend to feel a sense of comfort in their daily struggle to control their weight.

Public Profile

Figure 23:
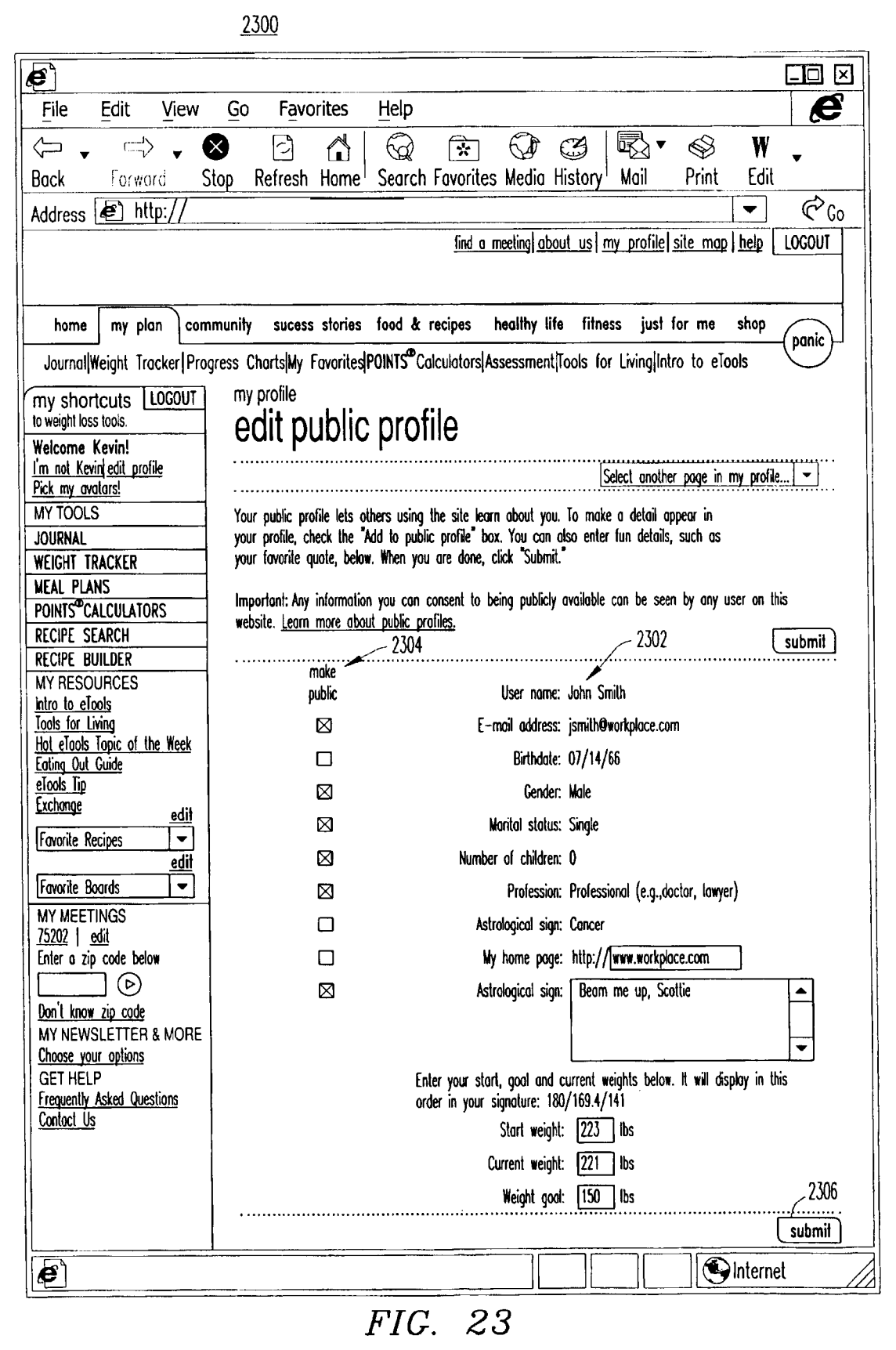

FIG. 23 is an exemplary web page 2300 that allows the user 110 to generate public profile information 2302 and selectively make that information public within the community utilizing the weight control software system utilizing check boxes 2304 corresponding therewith. The public profile information may include user name, e-mail address, birthdate, gender, marital status, profession, favorite recipe, food, activities, etc. Because the user 110 uses a user name, the identity of the user 110 may be protected. Additionally, other types of information may be entered, such as favorite quotes, how the user 110 spends his or her free time, and other items or expressions that the user 110 would like to share with the public community associated with the weight control software system provided by the weight control software provider 105. Because the weight control software system is oriented to weight control information, start weight, current weight, and weight goal also may be shared with the community. Additionally, by sharing such information, including current weight, the user 110 may feel more inspired to continue on with the weight control program 115. Upon completion of generating and selecting public profile information, the user 110 may submit the information to the community via a soft-button 2306.

Community Recipe Swap and Search

Figure 24A:
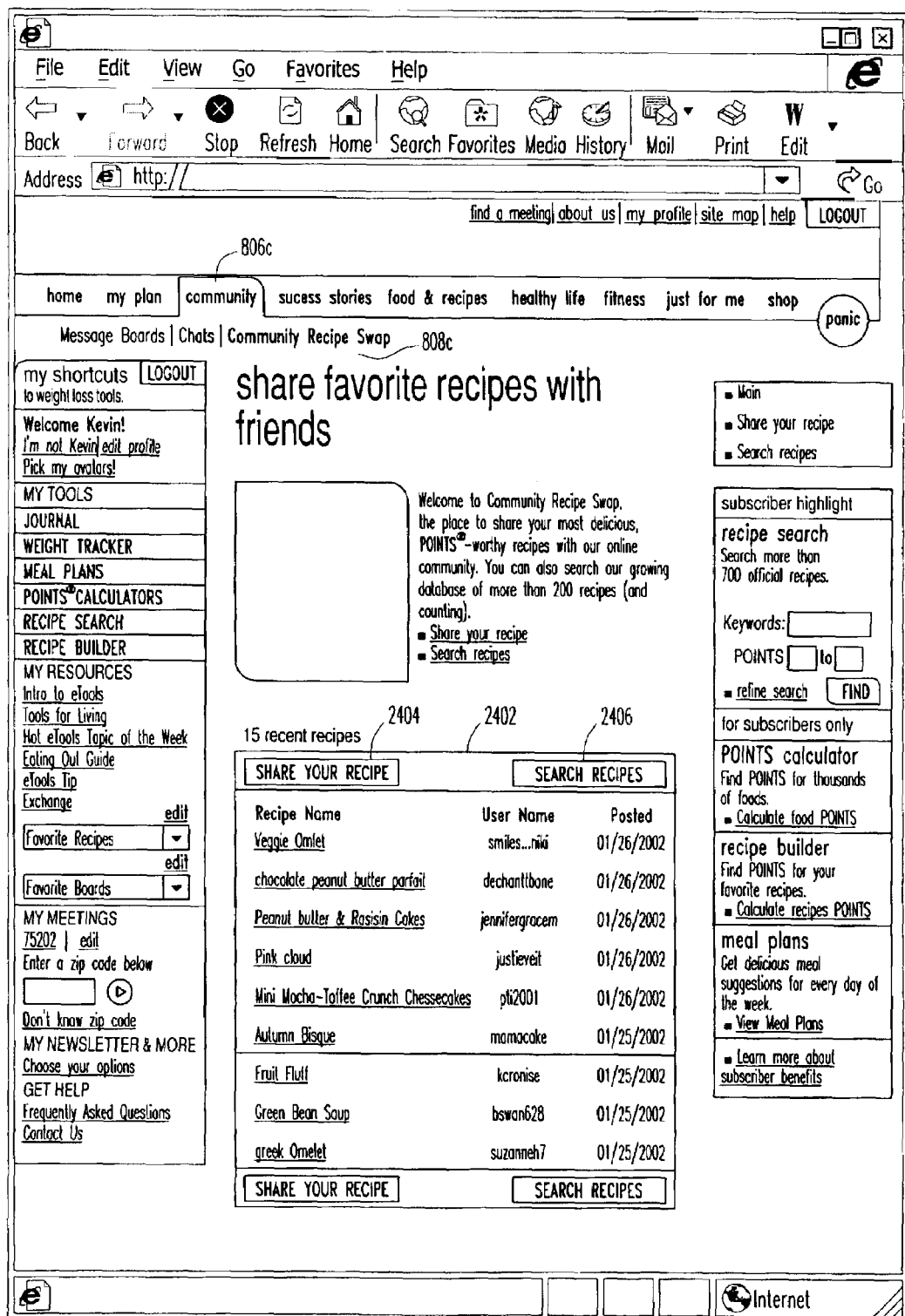
FIG. 24A is an exemplary web page illustrating the ability of the weight control software system of FIG. 2 to store and display shared recipes provided by other users of the weight control software system.

FIG. 24A is an exemplary web page 2400a for providing community information as enabled by the weight control software system. The community aspect of the weight control software system may be entered by selecting the "Community" site navigational element 806*c*. In the community, users 110 may find message boards, chat rooms, and a community recipe swap area. The "Community Recipe Swap" page navigational element 808*c* may be selected so that the user 110 may share and search for recipes provided by users 110. A recent recipe area 2402 provides the most recent recipes submitted to the community. As shown, a recipe name, user name, and date posted provides the user 110 with an indication as to the type of recipe that is posted. The user 110 may simply click on the recipe name operating as a hyperlink to view the recipe itself.

Figure 24B:
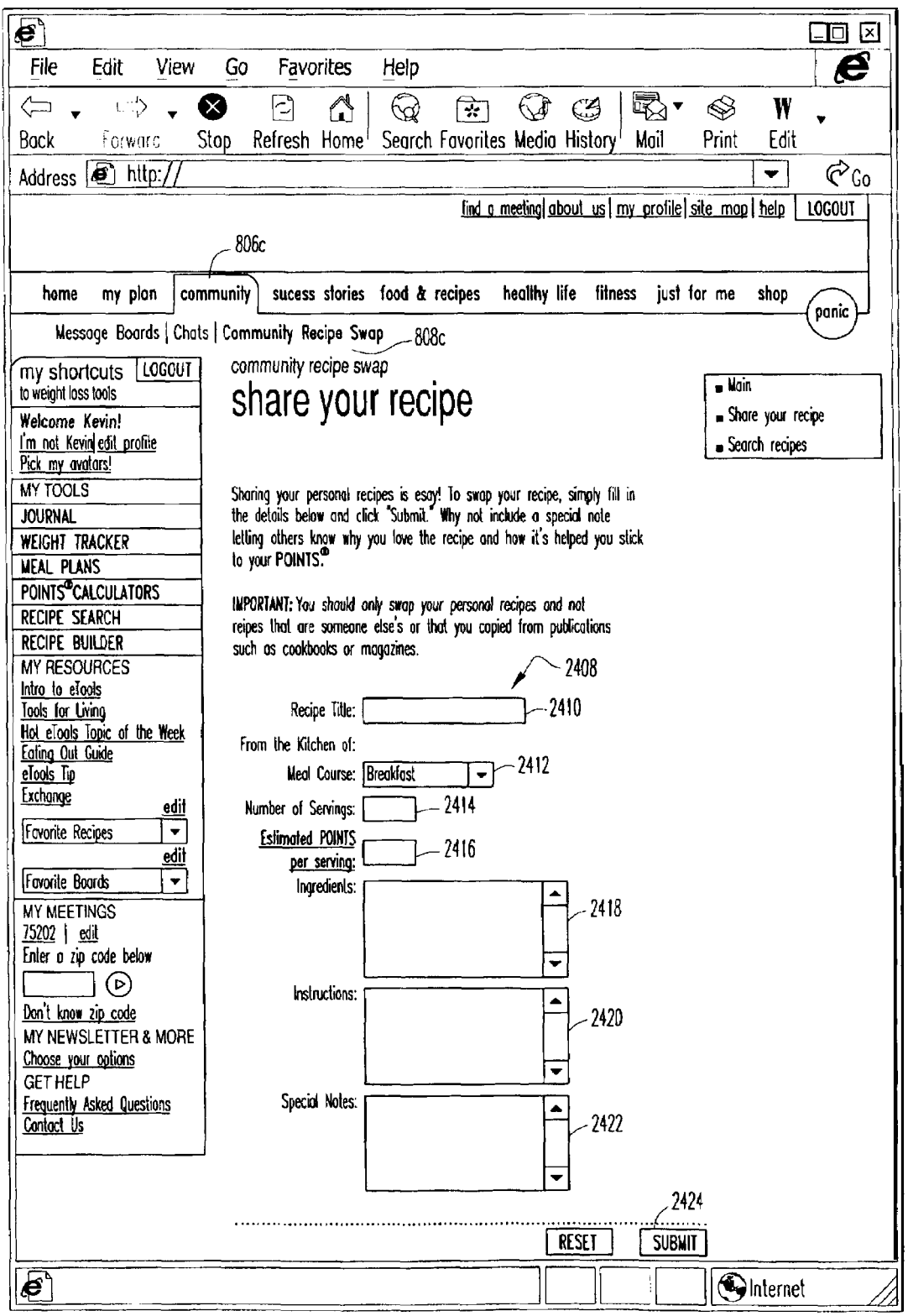
FIG. 24B is an exemplary web page illustrating the ability of a user of the weight control software system of FIG. 2 to input shared recipes and other criteria of FIG. 24A.

FIG. 24B is an exemplary web page 2400*b* that allows the user 110 to enter a recipe for sharing with the community of FIG. 24A. As indicated, a number of data entry elements 2408 are available for the user 110 to enter information regarding the recipe. Such recipe information may include a recipe title 2410, the meal course 2412 that the recipe is intended to be served, a number of servings 2414 that the recipe creates, an estimated food value per serving 2416 for the recipe based on the general rules of the weight control program 115, ingredients 2418, instructions for preparing the recipe 2420, and special notes 2422. Upon completion of entering the recipe information, a soft-button 2424 may be selected to submit the recipe to the community.

Figure 24C:
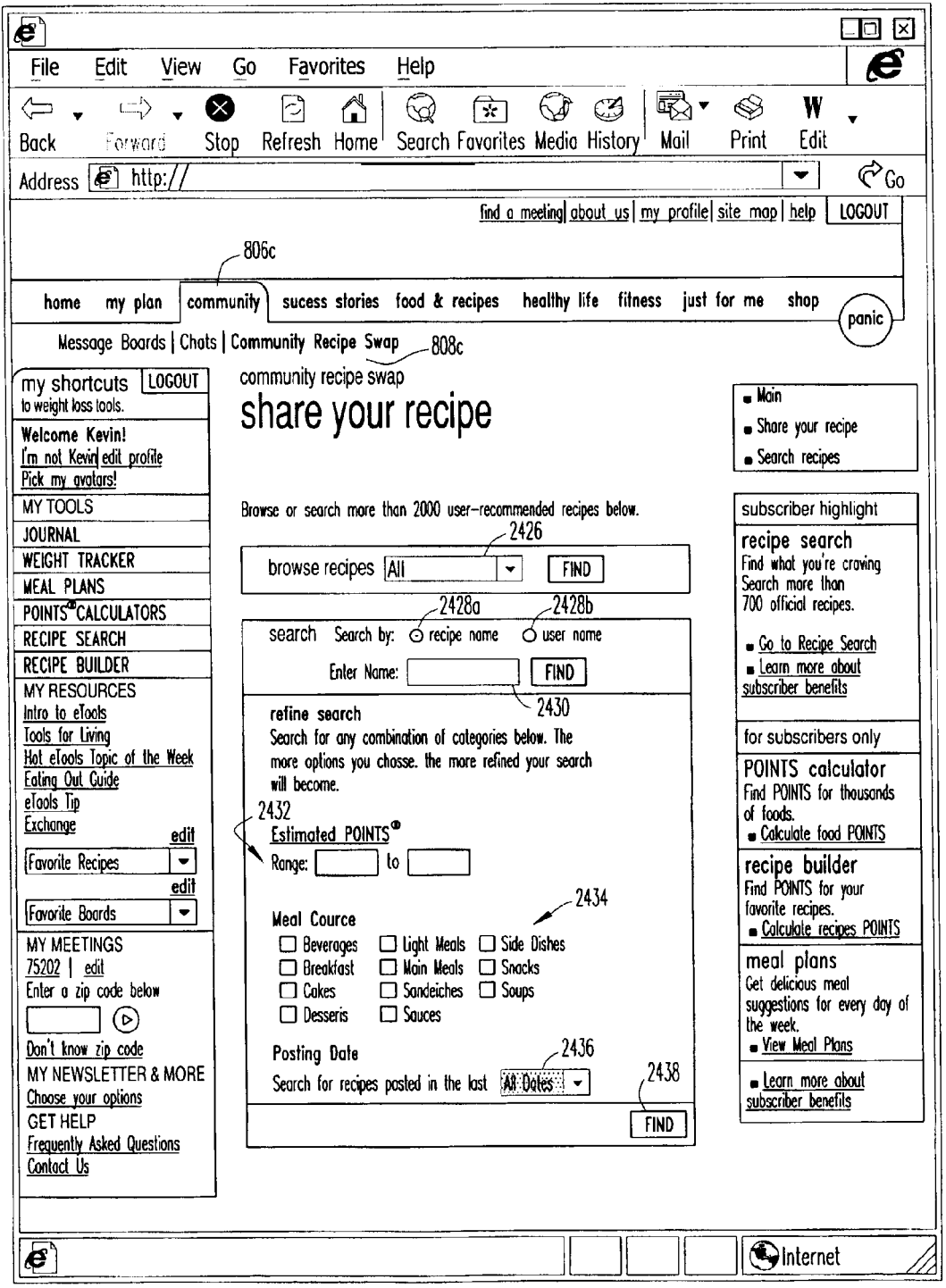
FIG. 24C is an exemplary web page illustrating the ability of users of the weight control software system of FIG. 2 to search shared recipes provided by other users of the weight control software system.

FIG. 24C is an exemplary web page 2400*c* for performing a community recipe search within the community of FIG. 24A. The search is operable to search information as supplied by users 110 of the community in accordance with the principles of the present invention. As shown, a "browse recipes" element 2426 is operable to limit the search to specific or all recipe categories. The user 110 may select a radio button 2428*a* or 2428*b* for searching specific recipe names or user names. In performing the search, the user 110 may enter a recipe name or user name into a text box 2430. To further narrow the search, others values may be submitted in entry fields 2432 based on the general rules of the weight control program 115 (FIG. 1). The user 110 also may select one or more meal courses to search using checked boxes 2434. Finally, posting dates may be selected via a pull-down menu 2436, which may include a range of dates, such as within the last two weeks. It should be understood that additional and/or alternative search refinement tools may be utilized in accordance with the principles of the present invention.

Upon selecting and entering the information for performing the search, the user 110 may select a soft-button 2438 to perform the search. The results of the search may list a number of recipes, which the user 110 may select and view by clicking on a hyperlink provided by the title. Details of the recipe may then be viewed and printed for the user 110 to utilize in accordance with the weight control program 115.

Because the weight control software system operates, at least in part, on the server 202, the opportunity for the users 110 to provide their personal information in a public forum may be accessed by others on the network 216. Additionally, the personal information may be applied to other community shared information, such as recipes.

The previous description is of preferred embodiments for implementing the principles of the present invention, and the scope of the invention should not necessarily be limited by this description. This invention, however, may be embodied in many different forms and should not be constructed as limited to the embodiments set forth herein; rather, these embodiments are provided so that this disclosure will be thorough and complete, and will fully convey the scope of the invention to those skilled in the art. The scope of the present invention is instead defined by the following claims.

What is claimed is:

1. A system for facilitating control of body weight, said system comprising:
   a computer;
   said computer stores a software program having instructions causing the computer to receive a profile from a user, the profile including initial body weight;
   said computer stores a software program having instructions causing the computer to determine an initial time-based plan as a function of the profile received from the user to facilitate control of body weight;
   said computer stores a software program having instructions causing the computer to selectively present to the user the time-based plan for facilitating control of body weight, wherein the time-based plan comprises the following two options:
   (a) a time-based structured meal plan schedule being a meal plan schedule automatically based on at least one component of the initial personal profile; and
   (b) a time-based non-structured meal plan schedule being a meal plan schedule based upon food selections received from the user;
   said computer stores a software program having instructions causing the computer to provide the user a mechanism by which the user selects between the two options presented to the user;
   said computer stores a software program having instructions causing the computer to receive an indication from the user indicative of whether the user selected the structured meal plan schedule option or the non-structured meal plan schedule option; and
   said computer stores a software program having instructions causing the computer to modify the initial time-based plan, in response to the option selected by the user.

2. The system according to claim 1, wherein said computer stores a software program having instructions causing the computer to receive cultural background of the user.

3. The system according to claim 1, wherein said computer stores a software program having instructions causing the computer to receive at least one characteristic associated with the user.

4. The system according to claim 3, wherein the characteristics include at least one of the following: health status, gender, height, age, health restrictions, religion, ethnicity, and blood type.

5. The system according to claim 4, where the health status includes at least one of diabetes and depression.

6. The system according to claim 3, wherein the characteristics include demographics.

7. The system according to claim 1, wherein the modified initial time-based plan is a function of heterogeneous data associated with the user.

8. The system according to claim 7, wherein the heterogeneous data includes user input and predetermined parameters associated with the time-based plan.

9. The system according to claim 7, wherein the user input includes at least one user-defined meal.

10. The system according to claim 1, wherein said software program having instructions causing the computer to selectively present to the user the time-based plan for facilitating control of body weight displays the time-based plan for the user to view.

11. The system according to claim 10, wherein the time-based plan is displayed in a calendar related format.

12. The system according to claim 10, wherein the user interacts with said computer using a computing device.

13. The system according to claim 12, wherein the computing device is a hand-held computing device.

14. The system according to claim 1, wherein the profile is received over a network.

15. A system for forming a meal plan based on a weight control program for a participant, said system comprising:
   a computer;
   said computer stores a software program having instructions causing the computer to receive an initial personal profile indicative of characteristics of the participant;
   said computer stores a software program having instructions causing the computer to establish a daily food consumption goal for the participant based on the initial personal profile;
   said computer stores a software program having instructions causing the computer to selectably present to the participant a time-based plan for facilitating control of body weight, wherein the time-based plan comprises the following two options:
      (a) a time-based structured meal plan schedule being a meal plan schedule automatically based on at least one component of the initial personal profile; and
      (b) a time-based non-structured meal plan schedule being a meal plan schedule based upon food selections received from the participant;
   said computer stores a software program having instructions causing the computer to provide the user a mechanism by which the user selects between the two options presented to the user;
   said computer stores a software program having instructions causing the computer to receive an indication from the participant indicative of whether the participant selected the structured meal plan schedule option or the non-structured meal plan schedule option;
   said computer stores a software program having instructions causing the computer to form, if the indication received from the participant indicates that the participant selected the structured meal plan option, a time-based meal plan schedule automatically based on at least one component of the initial personal profile, the meal plan schedule being consistent with the daily food consumption goal and utilizing foods having values associated therewith;
   said computer stores a software program having instructions causing the computer to form, if the indication received from the participant indicates that the participant selected the non-structured meal plan option, a time-based meal plan schedule based upon food selections received from the participant, the meal plan schedule being consistent with the daily food consumption goal and utilizing foods having values associated therewith; and
   said computer stores a software program having instructions causing the computer to provide the time-based meal plan schedule to the participant.

16. The system according to claim 15 wherein the meal plan schedule is alterable, and wherein:
   said computer stores a software program having instructions causing the computer to receive a modification to the alterable meal plan schedule; and
   said computer stores a software program having instructions causing the computer to apply the modification to the alterable meal plan schedule.

17. The system according to claim 15 wherein the meal plan schedule is formed utilizing pre-established food combinations having predetermined values associated therewith.

18. The system according to claim 15, wherein:
   said computer stores a software program having instructions causing the computer to receive an updated characteristic associated with the participant; and
   said computer stores a software program having instructions causing the computer to automatically alter the meal plan schedule based on the updated characteristic.

19. The system according to claim 18, wherein the updated characteristic includes the current weight of the participant.

20. The system according to claim 15, wherein the foods utilized to form the meal plan schedule are selected from a predetermined set of foods.

21. The system according to claim 20, wherein the predetermined set of foods is composed of a pre-established set of foods and a user supplied set of foods.

22. The system according to claim 21, wherein the pre-established set of foods include foods prepared by consumer restaurants.

23. The system according to claim 21, wherein the pre-established set of foods include branded foods.

24. The system according to claim 20, wherein at least some of the predetermined set of foods are meals.

25. The system according to claim 15, wherein said receiving and presenting are performed over a network.

26. The system according to claim 25, wherein the network is the Internet.

27. The system according to claim 15, wherein:
   said computer stores a software program having instructions causing the computer to generate a shopping list based on the meal plan schedule.

* * * * *